(12) United States Patent
Fuisz et al.

(10) Patent No.: US 10,195,142 B2
(45) Date of Patent: Feb. 5, 2019

(54) METHOD AND COMPOSITION FOR MAKING AN ORAL SOLUBLE FILM, CONTAINING AT LEAST ONE ACTIVE AGENT

(71) Applicants: Richard C. Fuisz, Bay Harbor Islands, FL (US); Joseph M. Fuisz, Surfside, FL (US)

(72) Inventors: Richard C. Fuisz, Bay Harbor Islands, FL (US); Joseph M. Fuisz, Surfside, FL (US)

( * ) Notice: Subject to any disclaimer, the term of this patent is extended or adjusted under 35 U.S.C. 154(b) by 0 days.

(21) Appl. No.: 15/866,729

(22) Filed: Jan. 10, 2018

(65) Prior Publication Data

US 2018/0296476 A1    Oct. 18, 2018

Related U.S. Application Data

(63) Continuation of application No. 15/486,331, filed on Apr. 13, 2017.

(51) Int. Cl.
*A61K 9/00* (2006.01)
*A61K 9/70* (2006.01)

(52) U.S. Cl.
CPC ............ *A61K 9/0056* (2013.01); *A61K 9/006* (2013.01); *A61K 9/7007* (2013.01)

(58) Field of Classification Search
CPC .... A61K 9/7007; A61K 9/006; A61K 9/0056; B29C 41/12
See application file for complete search history.

(56) References Cited

U.S. PATENT DOCUMENTS

| | | |
|---|---|---|
| 4,136,145 A | 1/1979 | Fuchs |
| 4,305,502 A | 12/1981 | Gregory et al. |
| 4,371,516 A | 2/1983 | Gregory et al. |
| 4,754,597 A | 7/1988 | Buxton |
| 4,758,598 A | 7/1988 | Gregory |
| 4,849,246 A | 7/1989 | Schmidt |
| 5,629,003 A | 5/1997 | Horstmann |

(Continued)

FOREIGN PATENT DOCUMENTS

AU    2012261557    *    1/2013    ............. A61K 31/00

OTHER PUBLICATIONS (http://www.matik.com/olbrich-answers-the-call-from-customers/), Jul. 30, 2015.

(Continued)

*Primary Examiner* — Kortney L. Klinkel
(74) *Attorney, Agent, or Firm* — Fitch, Even, Tabin & Flannery, LLP

(57) ABSTRACT

A method of making an oral soluble film, containing at least one active agent, includes providing a well of a predetermined size; depositing a film forming composition in the well; depositing an active agent composition in the well, the active agent composition being different than the film forming composition, the film forming composition and the active agent composition forming an admixture in the well; and drying the admixture in the well. Alternatively, the method includes providing a well of a predetermined size; depositing a film forming composition including at least one active agent in the well, the film forming composition having a viscosity below 2000 centipoise; and drying the film forming composition in the well.

5 Claims, 5 Drawing Sheets

(56) References Cited

U.S. PATENT DOCUMENTS

| | | | |
|---|---|---|---|
| 5,631,023 | A | 5/1997 | Kearney |
| 5,820,876 | A | 10/1998 | Hoffmann |
| 5,948,430 | A | 9/1999 | Zerbe et al. |
| 6,117,448 | A | 9/2000 | Hoffmann |
| 6,200,604 | B1 | 3/2001 | Pather et al. |
| 7,425,292 | B2 | 9/2008 | Yang |
| 7,666,337 | B2 | 2/2010 | Yang |
| 7,824,588 | B2 | 11/2010 | Yang |
| 7,897,080 | B2 | 3/2011 | Yang |
| 7,972,618 | B2 | 7/2011 | Fuisz |
| 8,017,150 | B2 | 9/2011 | Yang |
| 8,475,832 | B2 | 7/2013 | Myers et al. |
| 8,568,777 | B2 | 10/2013 | Fuisz |
| 8,603,514 | B2 | 12/2013 | Yang |
| 8,613,285 | B2 | 12/2013 | Fuisz |
| 8,617,589 | B2 | 12/2013 | Fuisz |
| 8,652,378 | B1 | 2/2014 | Yang |
| 8,685,437 | B2 | 2/2014 | Yang |
| 8,663,687 | B2 | 3/2014 | Myers |
| 8,696,637 | B2 | 4/2014 | Ross |
| 8,765,167 | B2 | 7/2014 | Myers et al. |
| 8,900,498 | B2 | 12/2014 | Yang |
| 8,906,277 | B2 | 12/2014 | Yang |
| 9,089,527 | B2 | 7/2015 | Hille |
| 9,108,340 | B2 | 8/2015 | Yang |
| 9,125,434 | B2 | 9/2015 | Fuisz |
| 9,150,341 | B2 | 10/2015 | Fuisz |
| 2003/0068378 | A1 | 4/2003 | Chen |
| 2003/0224044 | A1 | 12/2003 | Weibel |
| 2005/0037055 | A1 | 2/2005 | Yang |
| 2006/0207721 | A1 | 9/2006 | Slominski |
| 2006/0257463 | A1 | 11/2006 | Elsohly |
| 2009/0098192 | A1 | 4/2009 | Fuisz |
| 2011/0114532 | A1 | 5/2011 | Francois |
| 2011/0318390 | A1 | 12/2011 | Fuisz |
| 2014/0155483 | A1 | 6/2014 | Li |
| 2015/0071925 | A1 | 3/2015 | Larson |

OTHER PUBLICATIONS https://globenewswire.com/news-release/2016/04/04/825387/0/en/Cynapsus-Therapeutics-and-MonoSol-Rx-Announce-Global-IP-Licensing-Agreement.html) Apr. 4, 2016.

https://en.wikipedia.org/wiki/Orally_disintegrating_tablet edited Dec. 15, 2016.

Ilango, et al., In-Vitro Studies on Buccal Strips of Glibenclamide Using Chitosan, Indian J. Pharm. Sci, 1997, 59(5) p. 232-235.

Bonn et al, "Wetting and Spreading" 2009, 81(2), p. 739-805, 2009, 81(2), p. 739-805.

Krishnakumar, Wetting and Spreading Phenomena, available here: http://guava.physics.uiuc.edu/~nigel/courses/563/Essays_2010/PDF/Krishnakumar.pdf , May 13, 2010.

pp. 10-11, Case 1:14-cv-01574-RGA (District Court for Delaware) Watson's Post-Trial Brief Regarding Noninfringement of U.S. Pat. No. 8,900,497 filed Mar. 3, 2017.

Carboxymethylcellulose sodium salt from Sigma-Aldrich accessed via http://www.sigmaaldrich.com/catalog/product/sigma/c5678?lang=en&region=US on Aug. 24, 2017.

Dictionary definition of "admixture" (Oxford Dictionary accessed via https://en.oxforddictionaries.com/ definition/admixture on Oct. 31, 2017).

\* cited by examiner

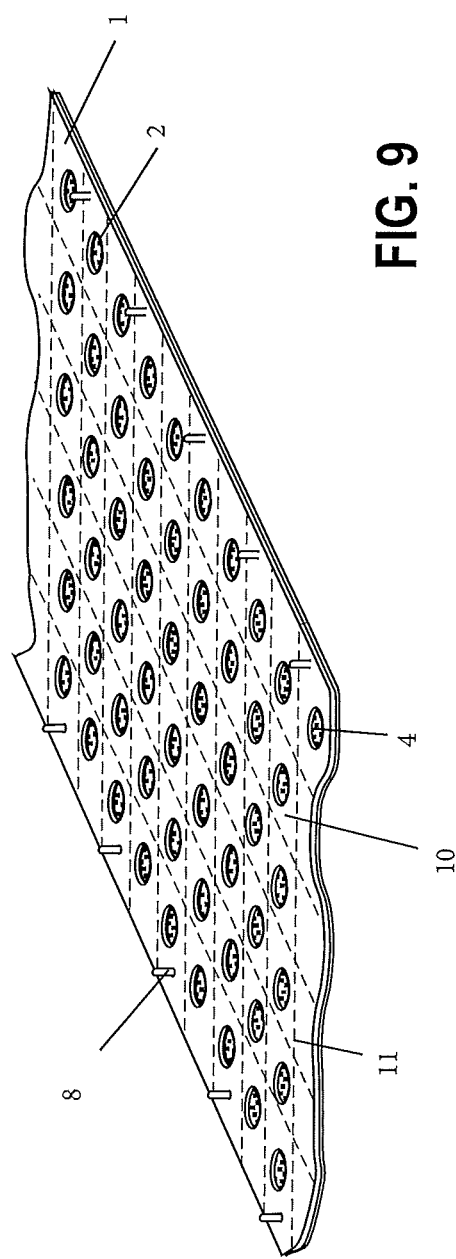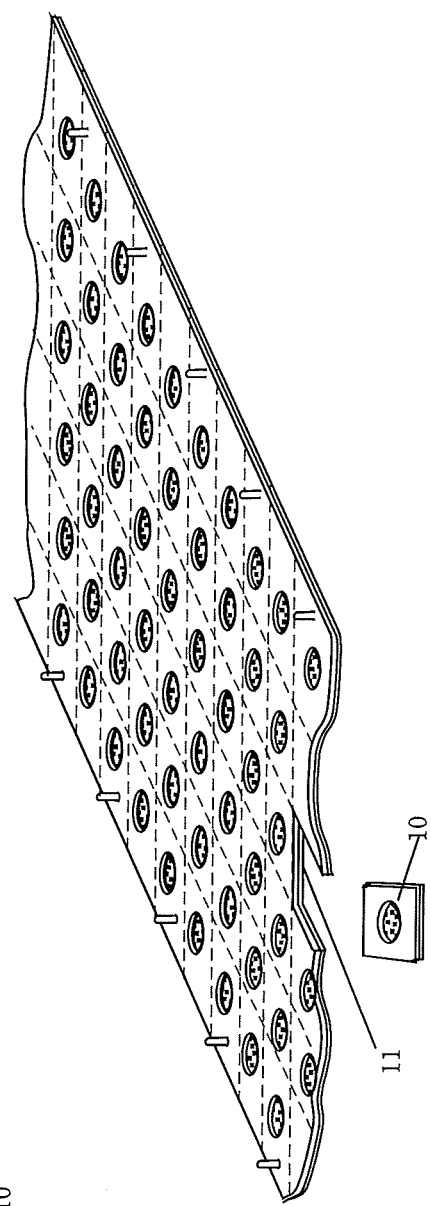

METHOD AND COMPOSITION FOR MAKING AN ORAL SOLUBLE FILM, CONTAINING AT LEAST ONE ACTIVE AGENT

CROSS-REFERENCE TO RELATED APPLICATION

This application is a continuation application of U.S. application Ser. No. 15/486,331, filed Apr. 13, 2017, the contents of which are incorporated herein by reference.

BACKGROUND OF THE INVENTION

Active ingredients, such as but not limited to drugs or pharmaceuticals, may be prepared in a tablet form to allow for accurate and consistent dosing. However, this form of preparing and dispensing medications has many disadvantages including a large proportion of adjuvants that must be added to obtain a size able to be handled, that a larger medication form requires additional storage space, and that dispensing includes counting the tablets which has a tendency for inaccuracy. In addition, many persons, estimated to be as much as 28% of the population, have difficulty swallowing tablets.

While tablets may be broken into smaller pieces or even crushed as a means of overcoming swallowing difficulties, this is not a suitable solution for many tablet or pill forms. For example, crushing or destroying the tablet or pill form to facilitate ingestion, alone or in admixture with food, may also destroy the controlled release properties, taste masking properties, or otherwise effect the pharmacokinetic properties of the drug.

As an alternative to tablets and pills, films may be used to carry active ingredients such as drugs, pharmaceuticals, dermals, cosmeceuticals, botanicals and the like.

However, historically films and the process of making drug delivery systems therefrom have suffered from a number of unfavorable characteristics, and the industry struggled to develop a commercially viable way to manufacture films for consumers.

Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water-soluble polymers, surfactants, flavors, sweeteners, plasticizers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and otic areas.

Commentators have suggested that examination of films made in accordance with the process disclosed in Fuchs, however, reveals that such films suffer from the aggregation or conglomeration of particles, i.e., self-aggregation, making them inherently non-uniform. See U.S. Pat. No. 8,658,437 (Yang et al., including the instant applicants) discussing Fuchs.

The formation of agglomerates randomly distributes the film components and any active present as well. When large dosages are involved, a small change in the dimensions of the film would lead to a large difference in the amount of active per film. If such films were to include low dosages of active, it is possible that portions of the film may be substantially devoid of any active.

What constitutes true uniformity in a cast film? It is usually not a true molecular uniformity but rather a dispersion of active in which a given size film falls within generally accepted guidelines.

Since sheets of film are usually cut into unit doses, certain doses may therefore be devoid of or contain an insufficient amount of active for the recommended treatment. Failure to achieve a high degree of accuracy with respect to the amount of active ingredient in the cut film can be harmful to the patient. For this reason, dosage forms formed by processes such as Fuchs, would not likely meet the stringent standards of governmental or regulatory agencies, such as the U.S. Federal Drug Administration ("FDA"), relating to the variation of active in dosage forms.

Currently, as required by various world regulatory authorities, dosage forms may not vary more than 10% in the amount of active present. When applied to dosage units based on films, this virtually mandates that uniformity of the drug in the film be present.

The problems of self-aggregation leading to non-uniformity of a film were addressed in U.S. Pat. No. 4,849,246 to Schmidt ("Schmidt"). Schmidt specifically pointed out that the methods disclosed by Fuchs did not provide a uniform film and recognized that that the creation of a non-uniform film necessarily prevents accurate dosing, which as discussed above is especially important in the pharmaceutical area.

Schmidt abandoned the idea that a mono-layer film, such as described by Fuchs, may provide an accurate dosage form and instead attempted to solve this problem by forming a multi-layered film. Schmidt forms an initial water soluble wet cast film. Next, "an aqueous coating material is prepared from the active ingredient, as well as starches, gelatins, glycerol and/or sorbitol, as well as optionally natural and/or synthetic resins and/or gums, and . . . the coating material is continuously applied by means of a roll coating process and in a precisely predetermined quantity (i.e via coating thickness) to at least one side of the support film . . . . With the aid of modern roll application processes the active ingredient-containing coating can be applied with a constant thickness, so that the necessary tolerances can be respected."

The Schmidt process is a multi-step process that adds expense and complexity and is not practical for commercial use and is in fact no more a guarantee of uniformity than is Fuchs. In fact, the Schmidt patent has expired without, to the personal knowledge of the instant inventors, any commercial use. Yang et al describe a related approach, wherein, in a cast film, "particles or particulates may be added to the film-forming composition or matrix after the composition or matrix is cast into a film. For example, particles may be added to the film 42 prior to the drying of the film 42. Particles may be controllably metered to the film and disposed onto the film through a suitable technique, such as through the use of a doctor blade (not shown) which is a device which marginally or softly touches the surface of the film and controllably disposes the particles onto the film surface" (U.S. Pat. No. 9,108,340).

Other U.S. patents directly addressed the problems of particle self-aggregation and non-uniformity inherent in conventional film forming techniques.

U.S. Pat. No. 5,629,003 to Horstmann et al. and U.S. Pat. No. 5,948,430 to Zerbe et al. incorporated additional ingredients, i.e. gel formers and polyhydric alcohols in wet cast films, respectively, to increase the viscosity of the film prior to drying.

In addition to the concerns associated with degradation of an active during extended exposure to moisture, the conventional drying methods themselves may be unable to provide uniform films.

The length of heat exposure during conventional processing, often referred to as the "heat history", and the manner in which such heat is applied, have a direct effect on the formation and morphology of the resultant film product.

Uniformity is particularly difficult to achieve via conventional drying methods where a relatively thicker film, which is well-suited for the incorporation of a drug active, is desired. Thicker uniform films are more difficult to achieve because the surfaces of the film and the inner portions of the film do not experience the same external conditions simultaneously during drying.

Thus according to commentators (U.S. Pat. No. 7,425,292), observation of relatively thick films made from such conventional processing shows a non-uniform structure caused by convection and intermolecular forces and may require moisture to remain flexible. The amount of free moisture can often interfere over time with the drug leading to potency issues and therefore inconsistency in the final product.

Put simply, the practitioner may walk a tightrope between moisture needed for desired mechanical attributes (flexibility of the self-supported film), and potentially deleterious consequences for chemical stability of the active ingredient associated with moisture.

Some discussion of mechanical attributes is important. In a conventional wet cast film, the film is coated on a substrate, dried, then rolled onto itself. The film is then processed, i.e. cut. Typically the edges are removed (trimmed), and the web (width) is cut into sub-width sections that can be accommodated by the film packaging machine (typically called "conversion" of the film). The film may or may not have been removed from its coating substrate, but either way requires sufficient mechanical strength to accommodate this processing.

If films lack the requisite pliability and tensile strength, they will tend to break during packaging causing substantial losses in process yield. Such breakage issues presumably led to the filing of a patent on methods of film splicing by Novartis (Slominski et al US 20060207721 A1). Some pliable, strong wet cast films, use polyethylene oxide (PEO) based compositions (See Yang et al. US 2005/0037055 A1). The strength of these films has led to the subsequent use of PEO in formulations commercially sold by Novartis. The reality is that physical strength and resulting breakage and process yield issues caused by breakage have been significant problems for many of the non-PEO wet cast films.

However, as regards pliability again the practitioner walks a tightrope. If the film is too pliable, it may stretch (elongate), particularly in the packaging stage where the film is under tension in the packaging lanes. Typically, in film packaging, the sub-roll of film is slit into lanes (each lane representing the width of the final dose) and then processed into unit dose foil packages. The final dosage is premised on relatively uniform distribution of drug in the film, and then cutting equally dimensioned pieces of films based on the calculated drug concentration. Hopefully that concentration is known ex ante (before coating), but it can also be determined ex post (after coating).

However, if the film is too pliable, it may stretch under tension (most commonly in the packaging stage here). The effect of such stretching will decrease the concentration of the drug in the film. For a "stretched" film, the given calculated dimensions (that did not anticipate stretch/elongation) will now yield an under-strength dosage form.

As a result, the formulator must provide a film that, when dried, is sufficiently pliable to accommodate conversion. At the same time, the film cannot be too pliable or it will stretch.

Even if the film's mechanical properties are sufficient for conversion and packaging, physical stability of the final dosage form over time is not necessarily assured.

The issue of physical stability is also an issue for wet cast films—expensive barrier packaging is often used as a matter of necessity. Still, physical stability is not always a given. Boots Chemists launched a Vitamin C strip manufactured by BioProgress in Tampa, Fla. that had to be removed from the shelves because it was crumbling in the package—earning the name "chips not strips."

This story is not unique—many projects have failed to move out from development to commercialization due to physical stability issues.

The formulator must accommodate these needs while still achieving the required performance when used (e.g. desired disintegration time, desired muco adhesion if a buccal film etc).

Conventional drying methods generally include the use of forced hot air using a drying oven, drying tunnel, and the like. The difficulty in achieving a uniform film is directly related to the rheological properties and the process of water evaporation in the film-forming composition as well as but not limited to the matters described above.

When the surface of an aqueous polymer solution is contacted with a high temperature air current, such as a film-forming composition passing through a hot air oven, the surface water is immediately evaporated and theoretically forming a polymer film or skin on the surface. This can seal the remainder of the aqueous film-forming composition beneath the surface, forming a barrier through which the remaining water must force itself as it is evaporated in order to achieve a dried film. As the temperature outside the film continues to increase, water vapor pressure builds up under the surface of the film, stretching the surface of the film, and ultimately ripping the film surface open allowing the water vapor to escape. As soon as the water vapor has escaped, the polymer film surface reforms, and this process is repeated, until the film is completely dried. The result of the repeated destruction and reformation of the film surface is observed as a "ripple effect" which produces an uneven, and often non-uniform film. Frequently, depending on the polymer, a surface will seal so tightly that the remaining water is difficult to remove, leading to very long drying times, higher temperatures, and higher energy costs.

Other factors, such as mixing techniques, also play a role in the manufacture of a pharmaceutical film, particularly a wet cast film, suitable for commercialization and regulatory approval. Air can be trapped in the composition during the mixing process or later during the film making process, which can leave voids in the film product as the moisture evaporates during the drying stage. The film may collapse around the voids resulting in an uneven film surface and therefore, non-uniformity of the final film product. Uniformity is still affected even if the voids in the film caused by air bubbles do not collapse. This situation also provides a non-uniform film in that the spaces, which are not uniformly distributed, are occupying area that would otherwise be occupied by the film composition and more importantly because there is a single mix in prior art casting, voids mean "no active present" here.

Some discussion of coating methods is needed, and the present inventors provide a good primer in U.S. Pat. No. 7,824,588 (Yang et al including the present inventors):

"Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating; curtain coating, or combinations thereof, especially when a multi-layered film is desired. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common."

"The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller."

"Offset Gravure is common, where the coating is deposited on an intermediate roller before transfer to the substrate."

"In the simple process of immersion or dip coating, the substrate is dipped into a bath of the coating, which is normally of a low viscosity to enable the coating to run back into the bath as the substrate emerges."

"In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod."

"In the slot die process, the coating is squeezed out by gravity or under pressure through a slot and onto the substrate. If the coating is 100% solids, the process is termed 'Extrusion.'"

The '588 continues: "The gap or knife over roll process relies on a coating being applied to the substrate which then passes through a 'gap' between a 'knife' and a support roller. As the coating and substrate pass through, the excess is scraped off. Air knife coating is where the coating is applied to the substrate and the excess is 'blown off' by a powerful jet from the air knife. This procedure is useful for aqueous coatings. In the curtain coating process, a bath with a slot in the base allows a continuous curtain of the coating to fall into the gap between two conveyors. The object to be coated is passed along the conveyor at a controlled speed and so receives the coating on its upper face."

Yang et al, including the present inventors, teach a "selection of a polymer or combination of polymers that will provide a desired viscosity, a film-forming process such as reverse roll coating, and a controlled, and desirably rapid, drying process which serves to maintain the uniform distribution of non-self-aggregated components without the necessary addition of gel formers or polyhydric alcohols." See U.S. Pat. No. 9,108,340.

Yang et al. strongly rely on viscosity in the pre-cast film solution to maintain drug content uniformity, and on said viscoelastic properties of the film composition to retard and avoid excess migration of drug during both the casting and drying process.

As U.S. Pat. No. 8,603,514 (Yang et al.) describes: "the viscosity of the liquid phase is critical and is desirably modified by customizing the liquid composition to a viscoelastic non-Newtonian fluid with low yield stress values. This is the equivalent of producing a high viscosity continuous phase at rest. Formation of a viscoelastic or a highly structured fluid phase provides additional resistive forces to particle sedimentation. Further, flocculation or aggregation can be controlled minimizing particle-particle interactions. The net effect would be the preservation of a homogeneous dispersed phase."

Yang et al. invoke Stokes' law to support this high viscosity approach. U.S. Pat. No. 8,603,514 describes: "One approach provided by the present invention is to balance the density of the particulate ($\rho_p$) and the liquid phase ($\rho_l$) and increase the viscosity of the liquid phase ($\mu$). For an isolated particle, Stokes law relates the terminal settling velocity (Vo) of a rigid spherical body of radius (r) in a viscous fluid, as follows: $V_o=(2gr^r)(\rho_p-\rho_l)/9\mu$"

Accordingly, claim 1 of U.S. Pat. No. 8,603,514 requires, inter alia, the following element concerning the viscosity of the film forming matrix: "matrix has a viscosity sufficient to aid in substantially maintaining non-self-aggregating uniformity of the active in the matrix."

The film compositions of Yang et al. (and other film artisans cited above) are so viscous that mechanical means (i.e. a physical means/physical object) in contact with the composition) are required to form a film by spreading the film composition on to the substrate. Put simply, the compositions are too viscous and have surface tension that is too high to pour. This is helpful in the coating process; after all, if the composition were too flowable it would roll/flow off the substrate. U.S. Pat. No. 8,906,277 (Yang et al.) describes the ability of the mechanical coating apparatus as providing the upper limit on viscosity of the film formulation: "the viscosity must not be too great as to hinder or prevent the chosen method of casting, which desirably includes reverse roll coating due to its ability to provide a film of substantially consistent thickness."

After the Yang et al. film compositions have been coated, Yang et al. describe a controlled drying process to avoid agglomeration of drug and resultant loss of content uniformity.

U.S. Pat. No. 8,603,514 (Yang et al.) describes: "In conventional oven drying methods, as the moisture trapped inside subsequently evaporates, the top surface is altered by being ripped open and then reformed. These complications are avoided by the present invention, and a uniform film is provided by drying the bottom surface of the film first or otherwise preventing the formation of polymer film formation (skin) on the top surface of the film prior to drying the depth of the film. This may be achieved by applying heat to the bottom surface of the film with substantially no top air flow, or alternatively by the introduction of controlled microwaves to evaporate the water or other polar solvent within the film, again with substantially no top air flow. Yet alternatively, drying may be achieved by using balanced fluid flow, such as balanced air flow, where the bottom and top air flows are controlled to provide a uniform film. In such a case, the air flow directed at the top of the film should not create a condition which would cause movement of particles present in the wet film, due to forces generated by the air currents. Additionally, air currents directed at the bottom of the film should desirably be controlled such that the film does not lift up due to forces from the air. Uncontrolled air currents, either above or below the film, can create non-uniformity in the final film products. The humidity level of the area surrounding the top surface may also be appropriately adjusted to prevent premature closure or skinning of the polymer surface."

"This manner of drying the films provides several advantages. Among these are the faster drying times and a more uniform surface of the film, as well as uniform distribution of components for any given area in the film. In addition, the faster drying time allows viscosity to quickly build within the film, further encouraging a uniform distribution of components and decrease in aggregation of components in the final film product."

High viscosity, high surface tension, and difficult flowability is a given in coating line systems. The picture at this link shows (www.matik.com/olbrich-answers-the-call-from-customers/) a standard Olbrich coating line. Olbrich is a leading manufacturer of coating equipment. The coating apparatus is physically below the drying tunnel, with the freshly coated substrate taking off at a severe (high) angle going up to the drying tunnel. When before any drying, it is necessary that the freshly coated film will not roll or flow off the substrate despite gravitational forces associated with this take off angle. It is important to note that drying methodology here is essential to uniformity. In the invention to be described here, the dose unit is confined and the drying method has substantially no role in dosage uniformity.

The Yang et al. approach has proved dominant in the marketplace for film. The most successful commercial orally soluble film product (measured by sales) is Suboxone® thin film, which has exceeded one billion in US sales in certain years. The FDA Orange Book references two patents of Yang and the present inventors in connection with Suboxone: U.S. Pat. No. 8,017,150 and U.S. Pat. No. 8,603,514. A third patent listed in the Orange Book for this product—U.S. Pat. No. 8,475,832 which deals with pH issues specific to Suboxone (as distinct from wet cast film manufacture generally)—has been found invalid by the District Court for Delaware (although this '832 pH patent may be under further judicial appeal).

To date, several sophisticated ANDA filers, including Watson Pharmaceuticals, TEVA Pharmaceuticals (the world's largest generic company with revenues exceeding twenty billion dollars) and PAR Pharmaceuticals, have been unable in judicial proceedings to show non-infringement (or invalidity) of the Suboxone-Orange Book listed patents. Watson and Par have been forbidden from launching generic film products, and a decision in the TEVA cases is expected shortly.

The next largest commercial orally soluble film success is the acquisition by Sunovion of Cynapsus for $624 million USD to acquire Cynapsus' apomorphine sublingual film. Cynapsus has a licensing arrangement to the same patent estate as Suboxone according to publicly available information (globenewswire.com/news-release/2016/04/04/825387/0/en/Cynapsus-Therapeutics-and-MonoSol-Rx-Announce-Global-IP-Licensing-Agreement.html). Moreover, the owner of the same patent estate recently sued BioDelivery Sciences for patent infringement for its Belbuca™ product, claiming infringement of another progeny of the same patent estate, U.S. Pat. No. 8,765,167 (Yang et al).

The applicants are not aware of any orally soluble film product with significant sales that does not license this patent estate.

The subject of loss (yield) and wet casting must be addressed. As we have discussed, wet cast film compositions are very viscous in the initial mixing stage. This viscosity, together with high surface tension, means that the film composition will experience loss with adhered product in the mixing apparatus and tubing from the mixing apparatus to the coater. Some mild loss may occur on the coating apparatus itself. There will be initial loss of product to bring the coater online until the product is running at standard parameters. Similarly, there will be loss at the end of a run bringing the coater off line (i.e. when too little material remains to maintain the coater running at standard parameters). As discussed, supra, product will be lost in the conversion stage by edge trimming, as well as cases where the width of usable web does not evenly divide by the input width required by the packaging line.

The packaging machine must be brought online (and offline at the end of a run), necessitating waste. Any breakage of film during packaging will result in waste in connection with lost product and restarting of the line. And so on—this is not a non-limitative list, but offers some insight into the innate wastefulness of the process The fact is that yields of wet cast film products are low, can result in substantial product loss, which is particularly concerning when casting expensive active pharmaceutical ingredients (API) (excipients being relative inexpensive by comparison to API). Loss can be higher than 25% of API, high as 35% API and even approaching 50% API loss. Such API loss may be acceptable for high value branded targets, but ultimately restricts the success of oral soluble film in competitive Rx, OTC and other consumer fields.

The oral soluble film format is generally preferred by consumers over orally disintegrating tablets, but the latter is currently less expensive to make (as compared with wet cast films). For example, generic ondansetron orally disintegrating tablets sell for $8/dose (www.drugs.com/price-guide/ondansetron#oral-tablet-disintegrating-4-mg); whereas ondansetron orally soluble film has a retail price of $35/dose (www.drugs.com/price-guide/zuplenz). In an era when drug prices are under fire publicly, and third party payers take a hard pencil to formulary reimbursement rates, this is a hard price differential to support. For orally soluble film to help deliver value to more patients, a more cost effective method of film manufacture is needed.

One way to avoid some of the product loss associated with wet casting is hot melt extrusion. Insofar as an extruder acts as a mixer and typically starts with substantially dry, non-aqueous compositions, hot melt extrusion avoids mixing loss associated with wet casting.

One of the present applicants has two US patents dealing with hot melt extrusion products and methods: U.S. Pat. No. 9,125,434 (Fuisz) and U.S. Pat. No. 8,613,285 (Fuisz). Hot melt extrusion offers other advantages including a much smaller manufacturing footprint than a wet casting line, and the ability to make longer lasting films/sheets than can be made with wet casting. However, hot melt extrusion as a process has its own limitations (vis a vis wet casting). A principal limitation of hot melt extrusion is a smaller menu of film formers that readily extrude, which makes formulation far more challenging (as compared with wet casting). Taste masking and controlled release may also be harder. Despite its strengths, applicants are not aware of any significant commercial film product made using hot melt extrusion, and applicants believe that the smaller menu of available film formers is a reason for this.

Discussion of the Zydis system is appropriate. The Zydis system is an orally disintegrating tablet, and is classified by the FDA as such (as distinct from orally soluble film). The Zydis system is well regarded for its rapid disintegration (relative to other orally disintegrating tablets), though the system has some limitations in terms of drug loading and taste masking. A primer on the history of orally disintegrating tablets, including reference to one of the present inventors, is available here: en.wikipedia.org/wiki/Orally_disintegrating_tablet.

The Zydis system, which is a freeze-dried tablet, is described in U.S. Pat. Nos. 4,371,516; 4,305,502; 4,758,598; 4,754,597, and 5,631,023, the teachings of all of which are incorporated herein by reference as if fully herein stated. The Zydis manufacturing method uses a pre-prepared liquid composition including a solvent, a granular therapeutic agent, and a gelatin containing carrier material.

The liquid composition (including the drug) is placed into one or more shaped depressions in a tray or mold to define liquid composition filled depressions. The liquid composition in the filled depressions is frozen, then the liquid portion of the liquid composition sublimed to define a solid medicament tablet. Sublimation is accomplished by freeze drying and can take several days. Thus, the tablet manufacturing process is not continuous; Zydis tablets-in-sublimation are stored in racks in a special chamber for sublimation. Only after sublimation can they be packaged.

Some mention of the CIMA orally disintegrating tablet is appropriate. The CIMA tablet uses a base-acid reaction (effervescence) to effect oral tablet disintegration. There is some support for the proposition that effervescence enhances buccal absorption. See U.S. Pat. No. 6,200,604 which is hereby incorporated by reference. Applicants are aware of no commercial oral soluble film product with effervescence, and attribute this to the practical difficulties of including acid and base in a wet cast film composition (without the product prematurely effervescing).

Finally, some mention of three dimensional printing is warranted. 3D printing has garnered much attention as a possible method for manufacturing pharmaceutical dosage forms. The products are printed layer by layer (using binding materials in between the layers of powder to adhere powder one layer to the other). The reality has failed to meet the hype, although a single printed dose product approval was obtained by Aprecia Pharmaceuticals for a product using its Zipdose technology licensed from MIT.

Applicants hereby incorporate by reference their oral film prior patents as if fully stated herein—these include: U.S. Pat. No. 7,425,292 (Thin film with non-self-aggregating uniform heterogeneity and drug delivery systems made therefrom); U.S. Pat. No. 7,666,337 (Polyethylene oxide-based films and drug delivery systems made therefrom); U.S. Pat. No. 7,824,588 (Method of making self-supporting therapeutic active-containing film); U.S. Pat. No. 7,897,080 (Polyethylene-oxide based films and drug delivery systems made therefrom); U.S. Pat. No. 7,972,618 (Edible water-soluble film containing a foam reducing flavoring agent); U.S. Pat. No. 8,017,150 (Polyethylene oxide-based films and drug delivery systems made therefrom); U.S. Pat. No. 8,568,777 (Packaged film dosage unit containing a complexate); U.S. Pat. No. 8,603,514 (Uniform films for rapid dissolve dosage form incorporating taste-masking compositions); U.S. Pat. No. 8,613,285 (Extrudable and extruded compositions for delivery of bioactive agents, method of making same and method of using same); U.S. Pat. No. 8,617,589 (Biocompatible film with variable cross-sectional properties); U.S. Pat. No. 8,652,378 (Uniform films for rapid dissolve dosage form incorporating taste-masking compositions); U.S. Pat. No. 8,663,687 (Film compositions for delivery of actives); U.S. Pat. No. 8,685,437 (Thin film with non-self-aggregating uniform heterogeneity and drug delivery systems made therefrom); U.S. Pat. No. 8,900,498 (Process for manufacturing a resulting multi-layer pharmaceutical film); U.S. Pat. No. 8,906,277 (Process for manufacturing a resulting pharmaceutical film); U.S. Pat. No. 9,108,340 (Process for manufacturing a resulting multi-layer pharmaceutical film); U.S. Pat. No. 9,125,434 (Smokeless tobacco product, smokeless tobacco product in the form of a sheet, extrudable tobacco composition); and U.S. Pat. No. 9,150,341 (Unit assembly and method of making same).

SUMMARY OF THE INVENTION

One aspect of the present invention relates to a method of making an oral soluble film, containing at least one active agent. The method includes providing a well of a predetermined size; depositing a film forming composition in the well; depositing an active agent composition in the well, the active agent composition being different than the film forming composition, the film forming composition and the active agent composition forming an admixture in the well; and drying the admixture in the well.

Depositing of the film forming composition in the well and depositing of the active agent composition in the well can be carried out sequentially or simultaneously from two separate depositiong devices. If sequential deposition is used, the active agent composition is preferably but not necessarily deposited in the well first and then the film forming composition is deposited in the well.

In another aspect of the invention, a method of making an oral soluble film, containing at least one active agent, includes providing a well of a predetermined size; depositing a film forming composition including at least one active agent in the well, the film forming composition having a viscosity below 2000 centipoise; and drying the film forming composition in the well.

In still another aspect of the invention, a film forming composition, suitable for making an oral soluble film, has sufficiently low viscosity and surface tension to flow into a film without mechanical intervention when deposited in a well.

BRIEF DESCRIPTION OF THE DRAWINGS

FIG. 8 is a perspective view showing a roll of wells, with films (and drug) deposited, films formed and dried, guideposts, and serration of individual doses within the roll of wells.

FIG. 9 is a perspective view showing a finished dosage form removed from a roll of wells, the breakage lines occurring at the lines of serration.

DETAILED DESCRIPTION OF THE INVENTION

Figure 1:
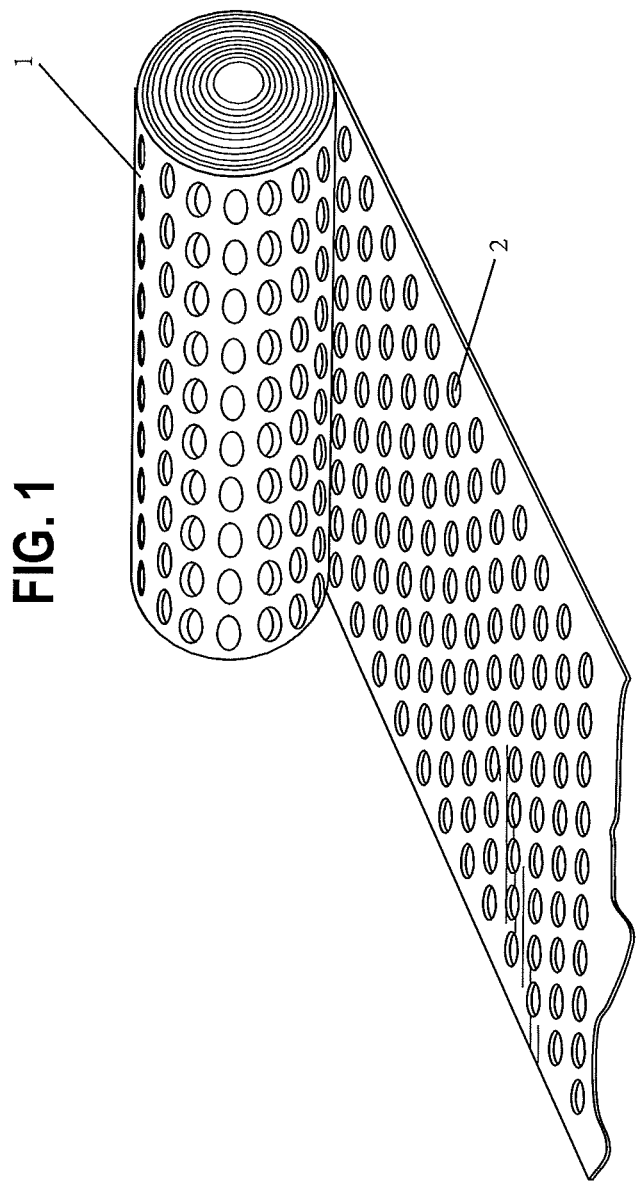
FIG. 1 is a perspective view of a roll of pre-formed molds or wells prior to filling.

One aspect of the present invention relates to a system for manufacturing an oral soluble film with an active agent, e.g., a pharmaceutical oral soluble film by the deposition of active and film former composition separately into a mold or well.

One aspect of the present invention relates to a system for manufacturing an oral soluble film with an active agent, e.g., a pharmaceutical oral soluble film by the deposition of active pharmaceutical agent(s) and film former together into a mold or well.

One aspect of the present invention relates to a system of continuous manufacture (formation of oral soluble films) and primary packaging of the oral soluble films.

One aspect of the present invention relates to a system for manufacturing an oral soluble film in which the active agent is deposited into a mold or well separately from the film former, and the drug binds or diffuses adequately mixes into the final, dried film matrix.

One aspect of present invention relates to a method of forming an oral soluble film with an active agent, e.g., a pharmaceutical oral soluble film without direct mechanical intervention to spread and/or coat and/or cast the composition into a film, such as by deposit of a sufficiently flowable film former composition into a well or mold and.

One aspect of the present invention relates to the use of a compressed gas to encourage and/or speed the flow of a film composition into a film shape in a mold or well.

One aspect of the present invention relates to the use of a compressed gas to encourage mixing of an active agent with a film former composition in a mold or well.

One aspect of the present invention relates to the use of brief vibration to encourage and/or speed up mixing of an active agent with a film former composition in a mold or well.

One aspect of the present invention relates to the use of brief vibration to encourage and/or speed up the flow of a film composition into a film well shape.

One aspect of the present invention relates to the manufacture of a film-sheet 1 to 40 mils (measured as dry thickness). This is non limiting and the methodology here allows for thick films and for dermal products.

One aspect of the present invention relates to a mold or well shape that is optimized for film formation by deposit method.

One aspect of the present invention replaces to mold or well material that is selected to be a suitable surface energy substrate to facilitate wetting and spreading of film former composition, i.e. low contact angle and/or surface tension.

One aspect of the present invention relates to pre-treating a mold or well with a surface active agent, a surfactant, or other agent to either promote flow of the film composition, and/or promote easier release of the dried film.

One aspect of the present invention relates to a composition suitable for making an oral soluble film where the viscosity and/or surface tension and/or interfacial tension of the composition (with the well/mold material, as applicable) is selected to promote flowability of said composition sufficient to form a film in a mold or well, and in certain embodiments to form such a film rapidly in such mold or well. This categorically teaches away from cast film art in that high viscosity is antithetical to successful formation of a deposit by precluding adequate flowability of the film former composition into a mold or well.

One aspect of the present invention relates to a film former composition with sufficient wettability to mix adequately in a mold or well with a separately deposited active.

One aspect of the present invention relates an oral soluble film made with one or more low molecular weight polymers as film formers One aspect of the present invention relates to a composition suitable for making an oral soluble film by the deposit method, where such composition is not capable of being wet cast into a film using traditional wet cast coating technologies (e.g. by three roll coater, or doctor blade).

One aspect of the present invention involves an alignment system to ensure the mold or well sheet is aligned with the top sheet. For example, aligning openings on the well sheet and the top sheet may be used so that through, for example, a pin type alignment each is properly oriented to the other.

One aspect of the present invention relates to a drying process that is suitable for the deposited composition to immediately flow into the shape of the mold or well prior to becoming too viscous to flow as a result of loss of solvent effecting viscosity increase.

One aspect of the present invention relates to the material of the mold or well selected that is suitable for the flow of the composition into a film.

One aspect of the present invention relates to the material of the mold or well selected to simultaneously allow the flow of the readily flowing composition while also allowing the dried material to be readily removed or peeled away from the well.

One aspect of the present invention relates to the design of the mold or well so that a user can readily remove the film.

One aspect of the present invention can allow the dosage unit to be sealed (primary packaging) on the same production line as the film is manufactured if desired. Alternatively, the dosage unit can be sealed on an adjacent packaging line. Standard packaging at a later time is also allowable.

One aspect of the invention relates to the substrate/laminate layer with pre-formed wells made at line or before line by blister forming methods.

One aspect of the present invention relates to the blisters being collapsible such that when the substrate layer is rolled up on itself, the film within it is loosened enabling easy subsequent removal by the user.

One aspect of the present invention relates to the manufacture and packaging of an oral soluble film with minimal composition and API loss (less than 30% preferably less than 20%, most preferably less than 10%).

One aspect of the present invention relates to a oral soluble film composition that has little or no yield stress. Such compositions are particularly well suited for the present invention (i.e. formation of an oral soluble film by deposit method).

One aspect of the invention involves a rolled adhesive onto the dried bottom sheet/mold/well edges, but excluding the interior of the sheet/mold/wells, so that top sheet can be adhered.

One aspect of the present invention relates to a film former composition with a viscosity below 2000 centipoise, preferably below 1000, more preferably below 600 centipoise, still more preferably below 300 centipoise. Such measurements, in the case of a Non-Newtonian film former composition, are measured at low shear rate, $<10\ s^{-1}$ One aspect of the present invention relates to the use of viscosity reducing agents in oral soluble film compositions. This teaches against the viscosity needed in traditional, wet cast films.

One aspect of the present invention relates to an oral soluble film with sufficiently uniform thickness and appearance for the user, with optional uniform distribution of components in the film. One embodiment of the present invention relates to an oral soluble film that does not have uniform distribution of active agent within the film.

One aspect of the present invention relates to an oral soluble film, made by deposit method, with <20% variability in height, preferably with <10% variability in height (measured from the thickest portion of the film to the thinnest portion, measured vertically).

One aspect of the present invention relates to an oral soluble film, made by deposit method, with one or more active agents, e.g., active pharmaceutical agents, wherein the content of said active pharmaceutical agent(s) varies less than 10% from the label claim, preferably less than 5%, preferably less than 2% from the label claim.

One aspect of the present invention relates to a multi-layer film made by deposit method.

One aspect of the present invention relates to the manufacture of a transdermal film, in whole or in part, by the deposit method.

In one aspect of the present invention, the unit dose, e.g., the top sheet thereof, is individually and preferably sequentially numbered or otherwise marked with a unique identification code so that the unit dose well can be traced in abuse prone drugs, or other drugs for which traceability is desired. This makes the unit dose pack of the present invention more advantageous than other forms of individual doses such as tablets that can not be individually numbered. A unit dose pack here can be. Hence with the opioid and other abuse drug, by the dispensing pharmacist simple recording that dose number, e.g., 1724-1744, was given to John Jones, if the package is ever involved in contraband it can be traced to origin.

One aspect of the invention is to allow for intermittent movement of the well substrate as opposed to the continuous movement demanded by the wet casting method.

Preferred embodiments of the present invention is described herein with reference to FIGS. 1-9, which schematically show examples of the method and system of the present invention. However, applicants' invention is not limited to the particular embodiments/examples shown in the figures.

FIG. 1 shows a roll 1 of pre-formed molds or wells 2 prior to filling by deposit. In other embodiments, the mold or well 2 may be formed on the production line itself from flat roll stock.

Figure 2:
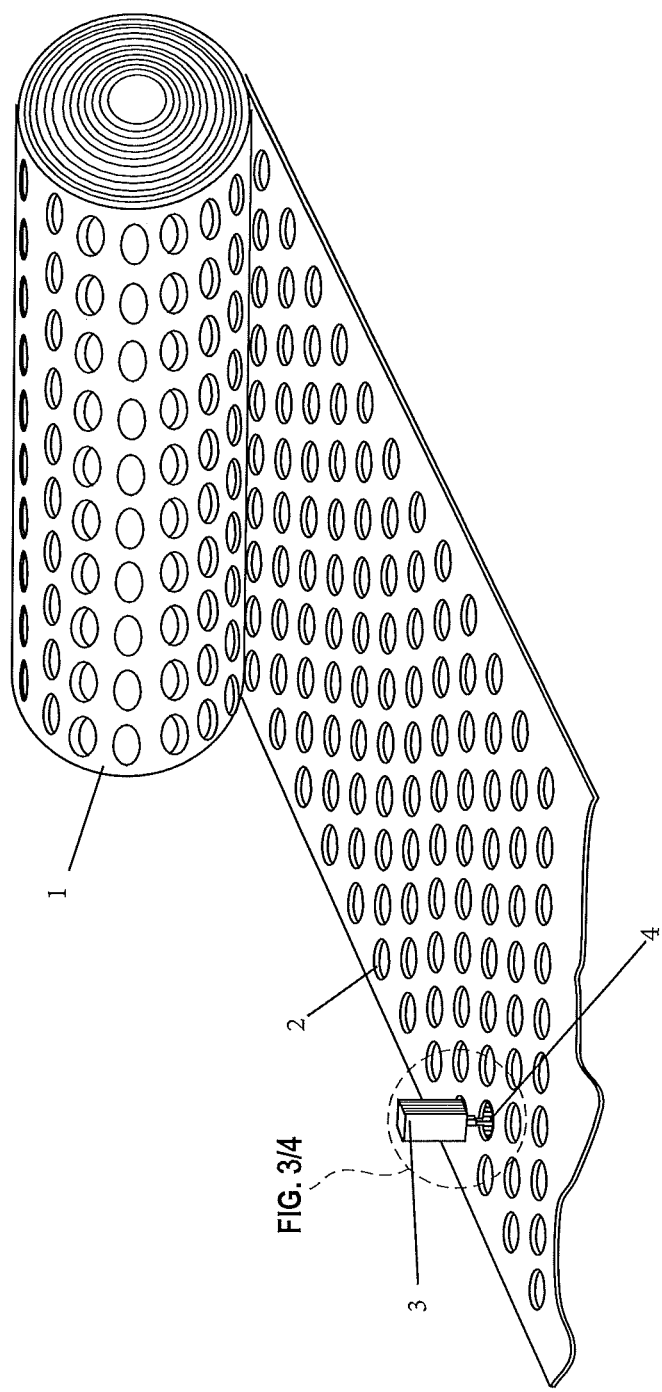
FIG. 2 is a perspective view showing a deposit device filling a well of the roll of pre-formed molds or wells.

FIG. 2 shows a deposit device 3, described in more detail hereinafter, filling a well. The deposit device 3 may be depositing film former composition, an active agent composition with optional excipients, or a film former composition complete with an active agent within it. In FIG. 2, the film former composition, the active agent composition with optional excipients, or a film former composition complete with an active agent are all designated generally with the reference numeral 4.

Figure 3:
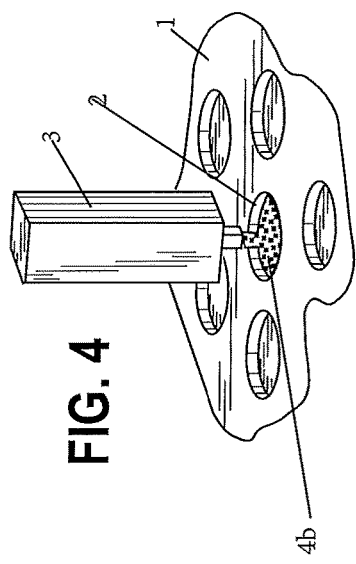
FIG. 3 is an enlarged view of a portion in FIG. 2 showing a deposit device filling a well with a film former composition.

FIG. 3 shows a deposit device 3 filling a well 2 with a film former composition 4a.

Figure 4:
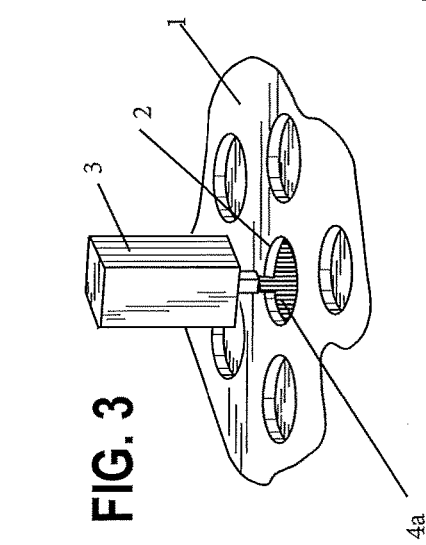
FIG. 4 is an enlarged view of a portion in FIG. 2 showing a deposit device filling a well with active pharmaceutical ingredient with optional excipients, in particulate form.

FIG. 4 shows a deposit device 3 filling a well 2 with a composition 4b including active ingredient(s) with optional excipients, in particulate form.

In one aspect of the present invention, a film forming composition 4a is deposited in each well 2 and an active agent composition 4b is deposited in each well 2, the active agent composition 4b being different than the film forming composition 4a. The film forming composition 4a and the active agent composition 4b form an admixture in the well 2. The film forming composition 4a and the active agent composition 4b may be separately deposited in the well 2 at the same time, e.g., through two separate deposit devices 3. Alternatively, depositing of the film forming composition 4a and the active agent composition 4b in each well 2 are carried out sequentially; in this embodiment, it is preferable but not necessary that the active agent composition 4a is first deposited in the well and then the film forming composition 4b is deposited in the well.

Figure 5:
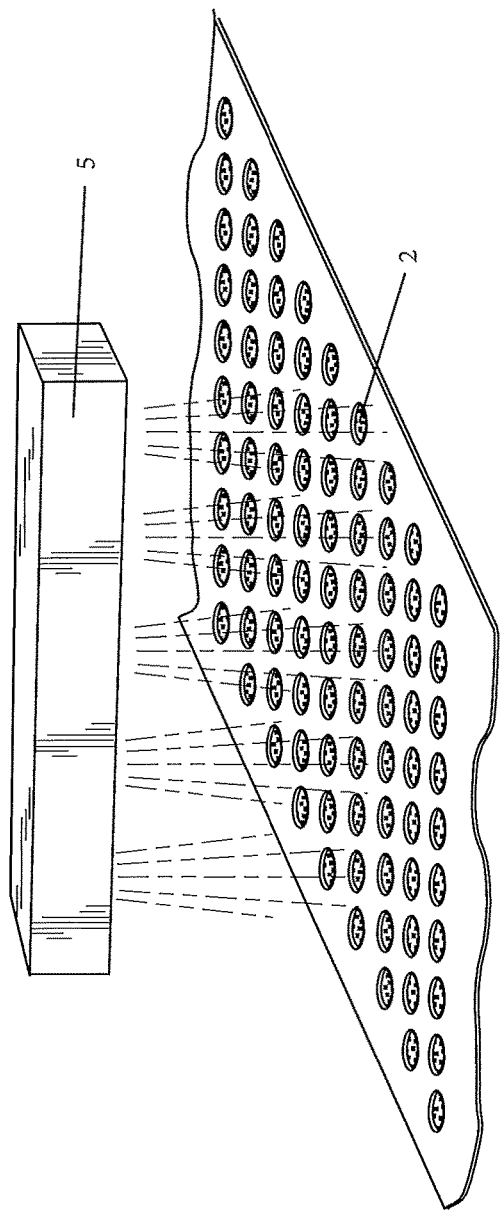
FIG. 5 is a perspective view showing a drying device deploying hot air currents from above the roll of film wells (which have been already filled).

FIG. 5 shows a drying device 5 deploying hot air currents from above the roll of film wells 2 (which have been already filled). In certain embodiments, drying occurs in a drying tunnel (here the tunnel is cut away for better visibility).

Figure 6:
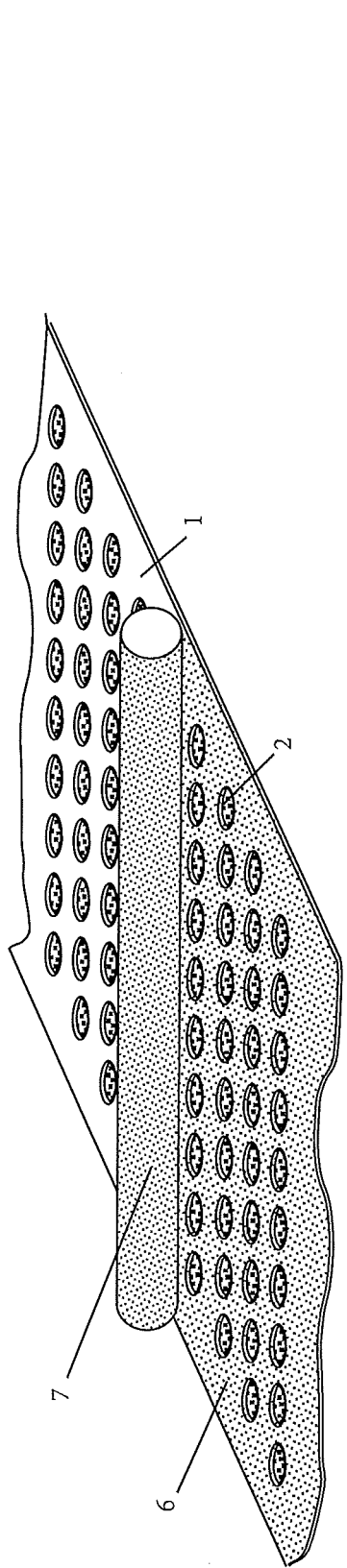
FIG. 6 is a perspective view showing adhesive being applied to well edges of bottom sheet.

FIG. 6 shows adhesive 6 being applied to well edges, i.e., to areas of the bottom sheet 1 outside the wells 2 by an applicator 7.

Figure 7:
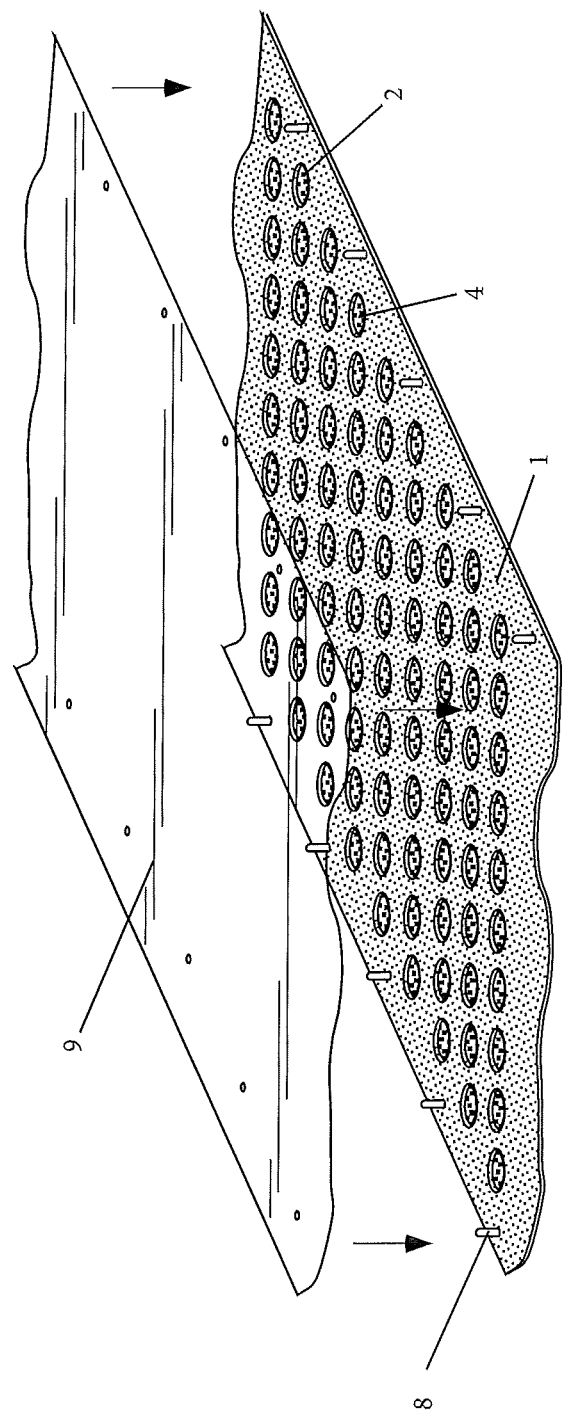
FIG. 7 is a perspective view showing a roll of wells, with films (and drug) deposited, films formed and dried, and guideposts inserted in the ends of the roll of wells for alignment of the top sheet which is placed over the bottom sheet.

FIG. 7 shows a roll 1 of wells 2, with films (and drug) 4 deposited, films formed and dried, and guideposts 8 inserted in the ends of the roll 1 of wells 2 for alignment of a top sheet 9 which is placed over the bottom sheet 1.

FIG. 8 shows a roll 1 of wells 2, with films (and drug) 4 deposited, films formed and dried, guideposts 8, and serration 11 of individual doses 10 within the roll of wells. Serration can occur in the roll stock prior to deposit of film composition 4 or after the manufacture of film 4.

FIG. 9 shows a finished dosage form 10 removed from a roll 1 of wells 2, the breakage lines occurring at the lines of serration 11.

A summary comparison of films made by certain embodiments of the deposit method of the present invention and films made by wet casting is provided below.

| Parameter/Attribute | Wet Cast Oral Soluble Film | Deposit Oral Soluble Film |
| --- | --- | --- |
| Viscosity of film former composition | High | Low |
| Flowability of film former composition | Low/None | High |
| Where Active Drug is added in process | Mixed with film former prior to coating on substrate | Deposited separately from film former composition (or optionally together) |
| Substrate in Continuous Motion | Coating must occur on substrate in continuous motion | Deposit in mold/well is not continuous (optionally continuous) |
| Coating substrate removal | Coating substrate must be removed in conversion prior to packaging | Substrate is typically not removed; deposited in final primary packaging |
| Angle of Flow of film former composition | High angle of flow of film former composition | Low angle of flow of film former composition |
| Stoke's Law employed to maintain drug content uniformity in film former composition | Stoke's Law employed to maintain drug content uniformity in film former composition | Stoke's Law has virtually no application where drug is deposited separately. |

| Parameter/Attribute | Wet Cast Oral Soluble Film | Deposit Oral Soluble Film |
|---|---|---|
| Controlled drying necessary for drug content uniformity | Controlled drying necessary for drug content uniformity | Controlled drying not necessary for drug content uniformity |
| Cutting of film specific size required to make final dosage form | Cutting of film specific size required to make final dosage form | Cutting of film not required to make final dosage form |
| Rapid drying required for drug content uniformity? | Rapid drying required for drug content uniformity | Rapid drying not required for drug content uniformity |
| Active Drug Waste (loss in process) | High API Waste | Low API Waste |
| Coating steps for Bi-layer film | Typically two separate steps of coating | Can be made in single deposit step. |
| Cost for Bi-layer | Typically expensive (two steps) | Marginally longer deposit step. Inexpensive |
| Low Dose Content Uniformity | Potentially challenging | Not challenging |
| Air bubbles, voids and surface defects create content uniformity issues | Air bubbles, voids and surface defects create content uniformity issues | Air bubbles, voids and surface defects do not create content uniformity issues |
| Separation of incompatible drug actives in a combination product | Difficult | Simple using separate deposit steps |

One aspect of the present invention is to enable film formulations which would have not have adequate mechanical properties for traditional oral soluble film manufacturing, i.e. ability to wind into a roll, ability to be trimmed and covered, ability to be released from substrate, and ability to be converted in a conventional film packaging machine (e.g. a Doyen Medipharm machine). For example, a formulation that has insufficient tensile strength for conventional conversion, or a formulation that has propensity for elongation under stress, would be unable to be converted using conventional means but is able to be manufactured using the deposit method.

The drug that is being deposited may be in the form of a powder or a solution in which case the drug solution in the bulk tank from which it is being deposited into wells in aliquots does not have to be stirred. However, it may also be a suspension of fine drug particles that may be continuously and vigorously stirred while the suspension is being deposited in aliquots into wells. Continuous stirring is generally not possible with viscous drug suspensions such as those used in formulations for continuous coating due to the induction of air into the mix which causes film defects and precludes collection of good and uniform product. In the deposit method, the low viscosity generally does not allow air bubbles to form in the film as they are immediately dissipated as the deposited liquid flows into the well as a thin layer.

Applicants teach against the fundamental theme of prior film art (Yang et al, Horstman, etc), namely, the use of high viscosity to (i) prevent migration of the active and preserve uniformity of dose content in the mixing stage, (ii) enable the required coating thickness of the film composition, and (iii) prevent migration of the active and preserve content uniformity in the drying stage. Instead, high viscosity (and surface tension) here work contrary to (i) the ability to deposit the film former composition into the well or mold, and (ii) the ability of the film former to flow (and reasonably rapidly and without mechanical intervention) into a film within the well or mold.

Deposit of a high viscosity film former composition such as those taught by Yang et al. in a well or mold will not generally result in a film at all, but rather simply a dollop-type shape of film former absent physical, mechanical intervention to spread the film former into a film (like a doctor blade, or other coating apparatus). Viscosity and surface tension simply prevent such compositions from flow, let alone sufficient flow to form a film.

It is important to note that to accurately dose and spread film former in a well, a relatively low viscosity is required (and surface tension), otherwise the material will refuse to spread in the well and simple form a dollop of material in part of the well.

Moreover, the embodiments where the drug active is separately deposited in the well or mold, high viscosity and lack of wetting can actually interfere with mixing of the drug active into the film matrix, thereby preventing adequate mixing of drug and film former composition from occurring.

High viscosity is also not needed to enable coating thickness of the composition; in the deposit method of the present invention the film composition can be readily deposited as high as the sides of the well or mold.

Film former and active are metered into the wells either singly or by multiple metering devices.

It is important to note that to accurately dose and spread film former in a well, a relatively viscosity low is required (and surface tension), otherwise the material will refuse to wet and spread in the well and simply form a dollop of material in part of the well.

Preferably, the after deposit, the film former composition will flow into a film in a well or mold within ninety seconds, preferably within sixty seconds, more preferably within twenty seconds, even more preferably within five seconds, and most preferably within one second. By flow into a film, Applicants mean that the film former composition will either reach the ends of the mold/well, or otherwise cease to flow.

This time is important as it will impact production line speed. Output of course may be improved by using a bank of feeders (filling multiple wells forward and horizontally at one time).

Both viscosity and surface tension are connected theoretically to inter-molecular forces, but they are still very different concepts.

Shear Stress is a force that acts on a fluid to cause flow and the viscosity determines velocity gradient. Viscosity is an intrinsic property of the fluid itself. Viscosity is the ratio of the shear stress tensor to the rate of deformation tensor.

Roughly speaking, viscosity determines how momentum is transported through a fluid during flow, as it is a measure of resistance to flow.

Contact angle acts not inside the substance, but only on its interfacial boundary with substance of another phase, even if nothing moves. It is not a property of the substance itself, but of a pair of these phases meeting at the boundary. Often the expression "contact angle of water" is used; but what is meant is contact angle of the pair water-air. Combinations water-glass or water-oil have different value of contact angle. Roughly speaking, contact angle says how much energy of interaction is stored when two chemical species are in mutual contact, even in equilibrium.

One way to think about the effective flowability of a film former composition for a given type of surface, is Young's equation. A drop of liquid when placed on a flat, homogenous solid surface comes to equilibrium, assuming a shape which minimizes the total free energy of the system. The angle between the liquid and the solid is called the contact angle, the angle being measured through the liquid. The contact angle may be calculated if the surface tension and interfacial tension are known, using Young's equation (see en.wikipedia.org/wiki/Wetting#Ideal_solid_surfaces, which is incorporated by reference as if fully stated herein, as retrieved on Mar. 26, 2017). For certain embodiments of the present invention, surface tension and interfacial tension are minimized to reduce the contact angle of the system. To wet the substrate well, the contact angle must be <90°.

One way to think about the rate of flow or spreading of the composition, is Tanner's law. Tanner's law teaches that the rate of spreading of a droplet is related inversely to the viscosity of the droplet. See Bonn et al, "Wetting and Spreading" (hereby incorporated by reference as if full set forth herein, and Krishnakumar, "Wetting and Spreading Phenomena, available here: guava.physics.uiuc.edu/~nigel/courses/563/Essays_2010/PDF/Krishnakumar.pdf and similarly hereby incorporated by reference as if fully set forth herein).

The preceding teaches away from Yang et al, wherein the film composition yields a high contact angle on the substrate, which allows for relatively thick non-flowing compositions. In fact, wet cast film coatings are so thick and unflowable, Watson has taken the position in its Suboxone ANDA litigation that its film coating should be understood to be a solid immediately after coating: "The physical evidence demonstrates that Watson's casting dispersion forms a viscolelastic solid when the forces of mixing and pumping cease, which happens before the initiation of drying . . . . The inspection video demonstrates that: (1) by the time Watson's casting dispersion travels up a steep incline for 30 seconds, and prior to any drying, it has already gained sufficient structure to "lock-in" and prevent migration of the active such that the casting dispersion does not flow backwards down the incline, as it would if it were a viscoelastic liquid; (2) Watson's films are cast as in discrete lanes at the width of the final film, which would not be possible if the casting dispersion were a viscoelastic liquid . . . " From Document 186, pp. 10-11, Case 1:14-cv-01574-RGA (District Court for Delaware). Thus Watson is stating to the Court that its film composition is simply not flowable at all, absent the mechanical intervention of the coating apparatus Film compositions of the present invention may be non-Newtonian or Newtonian. It should be noted that in the preferred embodiment, no mechanical force is applied to the film composition after deposit into the mold or well to encourage spreading/flowing of the film former composition. Accordingly, shear thinning or pseudo plastic attributes do not materially effect flowability in the well or mold since there is generally no mechanical source of shear stress other than gravity to effect a reduction in viscosity (as we would see in a coating apparatus).

It is contemplated in certain embodiments that shear force may be achieved by pressurized delivery of film former composition into the well (such shear being effected by the impact of the film former composition against the well). However, there are practical limitations on how much shear can be achieved in this manner with substantial absence of splatter outside of the well. Nozzle design can be optimized to reduce or mitigate splatter.

Film compositions of the present invention may have little or no yield stress. In certain embodiments, film compositions of the present invention will have insufficient yield stress to prevent flow on an incline greater than 45%, greater than 25% or even greater than 10%. In certain embodiments, the film composition of the present invention will have a yield stress <50 pa, preferably <30 pa, most preferably <15 pa.

The focus of the present invention teaches away from the thinking in the cast film art to use high yield stress to prevent sedimentation of drug particles and other components.

Continuous or Stuttered Manufacture

Embodiments of the present invention may employ continuous manufacture or stuttered (intermittent) manufacture.

In conventional wet casting, the substrate must be coated continuously. There is time (and waste) associated with bringing the coating process online to operating parameters with appropriate coating thickness. As a practical matter, the process must be continuous. This continuous coating typically implies long drying ovens.

Certain embodiments of the deposit method allows for a stuttered manufacturing process. One or more molds/wells is filled. At this time, the mold/well rollstock is stationary or moving (relative to the filler apparatus). After filling, the mold/well can be moved to a dryer. In certain embodiments, the filler may move with the mold/well so as to have no relative speed as between them during filling. Again, the molds or wells may continuously move through the dryer or it may be stationary in the dryer. The dryer apparatus may also be deployed after filling in a single place (i.e. without the mold/well moving).

In many embodiments, the deposit of film former composition and drug (and ensuing flowing into a wet film in the mold/well) is faster than the drying stage. Because deposit is non-continuous, in some embodiments, the mold/wells may be in stage blocks that can be placed into an oven on multiple levels. This allows for a small dryer footprint to accommodate relatively high production.

The stuttered option for deposit allows for a very efficient manufacturing in terms of footprint. Skilled artisans will appreciate the various configurations for deposit, drying, and packaging overlay on the molds/wells. A circular or other return layout between filler and dryer may be employed where a follow deposit is desired to be made to an initial dried film layer.

Methods of Deposit

Generally, the materials will be deposited in the well or mold using a flowmeter enabled feeder (any suitable flowmeter and feeder may be employed). The flowmeter may measure mass and/or volumetric flow rate of a liquid or solid. K-tron is a non-limitative example of a suitable feeder. Any suitable apparatus that can reliability deposit filmer former composition or drug may be employed.

Apart from gravity feed, pumps may be employed to feed the material into the well. Speed of deposit is important for line speed/product output. Moreover, it may be desirable to inject material into the mold or well with some additional force beyond gravitational force.

A bank of feeders may be employed to allow for a number of wells/molds across (and forwards) to be simultaneously. Optionally, the bank of feeders may source from a single mother tank.

Where the drug is deposited separately, multiple feeders may be employed: one to supply an active drug (or drug combination) (optionally with one or more suitable excipients), and one to supply the film former composition.

If the active drug is a particle, the active drug may be delivered in dry powder form, or in solution (where soluble), suspension or emulsion. One advantage of dry powder form is to avoid the time during which the drug active is in contact with liquid (which can avoid problems with crystallization, drug stability, and the degradation of taste masking or controlled release systems).

Where the drug is soluble, certain embodiments may use a pH for the drug solution optimized for solubility (where pH buffer of the film former composition uses a different, stronger buffer to control the ultimate pH of the dosage form). The drug may be solubilized in any appropriate polar or non-polar solvent.

One advantage of a solution, suspension or emulsion, is to promote mixing of the pharmaceutically active agent with the film former composition, though it is demonstrated in examples below that dry particles can be adequately mixed with separately metered film former compositions.

The feeders may employ nozzles that are optimized to promote mixing. For example, the nozzle may be selected to broadly disperse material in the well. The nozzle may be aimed to initiate flow in the well or mold. Where the drug is administered separately, the nozzle depositing the drug and the nozzle depositing the film former composition may be aimed in a complimentary fashion to promote mixing of the two. As a non-limitative example, the nozzles may direct the flow of the film former composition and drug in opposite directions. Nozzles may have a design to encourage mixing. In addition, nozzles may be used that have a spray pattern which is matched or otherwise calibrated to the well dimension.

Where the drug is administered separately from the film former composition, the two may be deposited in sequence, or contemporaneously (in which case the deposit rates may be calibrated in terms of time), or metered in a rotating sequence (for example and without limitation, film former composition, drug: drug, film former composition).

Where delivered separately, each of the film former composition and the drug (be it in particulate, solution, suspension, emulsion etc) may optionally be paired with any suitable excipient.

Separate administration of film former composition from drug is the preferred embodiment. First, the viscosities of a film former composition to resist sedimentation of the active would be too high for the film-by-deposit method of the present invention. Second, even soluble drugs may tend to come out of solubility in the film former composition, due to the relative low levels of solvent, interaction with other materials in the film former composition, and other chemical processes. Generally, greater control and reliability of target dose deposit is associated with separate administration of drug.

Drugs may be separately and sequentially deposited in the case of incompatible drugs. For example, multiple layers may deposited, each with a different active. In certain embodiments, the second layer is deposited after the preceding lawyer has been dried. In some instances, the active and the film former and the excipients could all be in one mix and dispensed simultaneously through a single deposition from one deposer. In embodiments in which the second layer deposited after the first layer is dried, it could be on top and include, without limitation, active in sustained release form, taste masking, absorption enhancers, pH modifiers and other modifiers such as an acid and base to produce effervescence. When introduced however, with things like coloring the mix, the top could become the bottom re the patient directions.

It may be desirable to heat the film former composition to promote flowability prior to, or after deposited in the mold or well. Attention must be paid to degradation temperature, and the sustained temperature should not exceed the drugs's known degradation temperature. Temperature increase will tend to decrease viscosity and surface tension provided that the solvent is not permitted to escape (or otherwise not replenished).

The Well or Mold

In this application, we use the terms well and mold interchangeably.

The well or mold will generally be of suitable depth to contain the wet height of the desired film composition. As a practical matter, the film tends to reduce in thickness when dried. The well or mold may be pretreated with silicone, hydrophobic agents, or and other suitable material that promotes flow of the film composition and/or promotes release of the final dry film from the well or mold.

Round shapes of the well or mold are desirable, but non limiting, to form a round film. Circular shapes may be particularly desirable but square or rectangular forms are also possible. In the case of circular shapes, the film composition can be deposited in the center and flow outward. Any regular or irregular polygonal shape may also be possible. The mold or well may also be shaped for form three dimensional attributes on the bottom of the film.

The sides of the well or mold may be perpendicular, angled (outward from the planar bottom surface).

In certain embodiments, the well or mold is sufficiently flexible to allow a consumer to readily push the bottom of the well or mold up to present the film for easy access by the patient.

The well or mold material must be able to withstand drying temperatures of the drying process.

In certain embodiments, the mold or well is formed using mechanical tools (including without limitation, dies or stamps) as part of the continuous production process. For example the process may begin with a suitable, flexible rollstock in which the required wells are formed by a die tooling, such formation occurring prior to the deposit step in production.

In certain embodiments, the well or mold is sufficiently flexible and shallow enough to allow for the well or mold, after deposit, drying, and application of top sheet, to be rolled onto itself after drying. In other embodiments, the wells or molds or cut in blocks and stacked after application of the top sheet.

In most embodiments, the area of the mold or well defines the dimensions of the film. The mold or well is of fixed size. Generally, the mold or well with have a deposit surface of 2 square inches or less, preferably 1.5 square inches or less. Larger size are possible smaller sizes are preferred for comfort (in oral use), as well as to speed flow of the film composition to ultimate dimensions (i.e. a shorter distance to travel).

In certain embodiments, the molds or wells are fixed and the dried films are removed from said molds or wells which can then be reused.

In certain embodiments, the well or mold is made of metal foil, e.g., aluminum foil, or plastics, and combinations. Suitable materials may include, without limitation, polyvinyl chloride (PVC), polyethylene (PE), polypropylene (PP), polyester (PET), Polyvinylidene chloride (PVDC), Polychlorotrifluoro ethylene (PCTFE), cyclic olefin copolymers (COC) or polymers (COP), monomer ethylene (LDPE), Aclar, paper aluminum combinations, paper/PET/aluminum laminates, and other aluminum based laminates.

The Drying Process

Typically, the film is dried in the well or mold. Drying can occur with little consideration to migration of drug, unlike traditional film wet casting. The only practical consideration relates to enabling suitable mixing of the drug (in embodiments where the drug is separately administered from the film forming composition) into the film matrix.

Generally, consideration is given to speed, energy use and efficiency of drying, sufficient evacuation of solvent, and minimizing visible imperfections on the film.

Another important distinction, is drying time. In conventional wet casting, the aim is to rapidly dry the film to prevent migration of the active. For example, US '277 claim 1 describes "rapidly increasing the viscosity of said polymer matrix upon initiation of drying within about the first 4 minutes to maintain said uniform distribution of said pharmaceutical active by locking-in or substantially preventing migration of said pharmaceutical active."

Because the present invention meters the desired drug loading, there is no concern for agglomeration of drug from a content uniformity perspective. This allows for longer drying times. Such longer drying times can serve a variety of purposes, and can be particularly useful in connection thicker films or for actives that are particularly heat sensitive.

At the same time, more rapid drying times can be effected, without concern for disruptions to the top of the film surface.

Since cast film requires viscosity rapidly for uniformity of dosage, specific drying is described, oriented towards early bottom drying to prevent volatile release of solvent and disruption of uniformity. On the other hand, the system herein described does not have that requirement and hence simplified top drying, not limited to air, infrared etc. is very workable.

Taste Masking

All currently known (and future) methods of taste masking may be employed, including flavors, sweeteners, bitter masking agents, coated particles, ion exchange resins and other methods. A significant advantage of the present method is that the drug residence time can be minimized.

For example, where the drug is deposited separately from the film former, the drug can be completely without solvent. As a non limitative example, drug in an ion exchange complex can be metered into the well, or coated drug particles. This means that the only exposure to water (or other solvent) in the film forming process is the brief period when the drug is mixed with the film former composition until the solvent is dried.

Preferably, taste masked particles have a particle size with a diameter no greater than the dried height of the film itself. Consideration may also be given to mouthfeel. Preferably for mouthfeel particle size is below 300 microns, preferably below 200 microns most preferably below 100 microns.

It is noted that the deposit method of making films taught herein offers a particular advantage for taste masking, namely, the ability to minimize the time that controlled release drug particles (or complexes) are subject to a solvent.

In the method where the drug active is deposited separately from the film former composition, the drug particles (or complexes) are exposed to the solvent used to hydrate the film former for the very brief period between deposit of the drug particles (or complexes) and the time it takes to substantially remove the solvent by drying. This can have also advantages even where neat drug is used (e.g. to avoid a drug from partially solubilizing in the solvent and then crystallizing).

Accordingly, total residence time of the drug with liquid solvent may be less than fifteen minutes, preferably less than ten minutes, more preferably less than five minutes, and most preferably less than two minutes. Such low residence times are also of utility with taste masked or controlled release drug particles or complexes.

Controlled Release

The term "controlled release" is intended to mean the release of active at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed drug releases are also contemplated. A non limiting example would be where immediate acting drug is separately deposited together with or separate from the film former and a second or third deposit of drug with a differing release pattern is added.

The polymers that are chosen for the films of the present invention may also be chosen to allow for controlled disintegration of the active. This may be achieved by providing a substantially water insoluble film that incorporates an active that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active inside the digestive system upon consumption.

Films that provide a controlled release of the active are particularly useful for buccal, gingival, sublingual and vaginal applications. The films of the present invention are particularly useful where mucosal membranes or mucosal fluid is present due to their ability to readily wet and adhere to these areas. In addition, this invention would allow for a barrier layer to be metered in the well at some time after the initial well contents have solidified, thus making a buccal/barrier product. Such barrier layer (soluble or insoluble) may also be deposited first in certain embodiments.

The convenience of administering a single dose of a medication which releases active ingredients in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of sustained release dosage forms are well known. However, the preparation of a film that provides the controlled release of an active has advantages in addition to those well-known for controlled release tablets. For example, thin films are difficult to inadvertently aspirate and provide an increased patient compliance because they need not be swallowed like a tablet. Moreover, certain embodiments of the inventive films are designed to adhere to the buccal cavity and tongue, where they controllably dissolve. Furthermore, thin films may not be crushed in the manner of controlled release tablets which is a problem leading to abuse of drugs such as Oxycontin. Furthermore, as mentioned the sequential numbering of the unit dose wells allows for identification of a source of the abusive drugs, providing the pharmacist notes the identification indicia during dispensing.

The actives employed in the present invention may be incorporated into the film compositions of the present invention in a controlled release form. For example, particles of drug may be coated with polymers such as ethyl cellulose or polymethacrylate, commercially available under brand names such as Aquacoat ECD and Eudragit E-100, respectively. Solutions of drug may also be absorbed on such polymer materials and incorporated into the inventive film compositions. Other components such as fats and waxes, as well as sweeteners and/or flavors may also be employed in such controlled release compositions.

Film Thickness

Films are typically understood to be up to 10 mils in thickness (final product as dried), and above ten mils the product is referred to in a sheet. For ease of reference, references herein to film are understood to apply film (sheet) both up to, and beyond 10 mils in thickness. Films of the present invention may be 1-200 mils, preferably 5-20 mils, most preferably 5 to 15 mils. Thickness may be augmented above the foregoing thicknesses, including without limitation, for dermal use of the end product.

Guided Placement

The mold or well becomes the bottom of the final package and only requires the guided placement of a top sheet which completes the package and the dose unit is merely cut or weakened from the dosage next to it. By guided placement is meant that markers, physical or printed align the top sheet so that cutting of the final unit dosage unit aligns readily with the cutter or perforator. In addition, full labeling requirements may be resident on the top sheet and bottom wells.

Content Uniformity

The most substantial problem in cast films is the difficulty to have a uniform dosage in a film which is cast with the active diluted by a large number of film formers and other additives plus a time profile for casting plus the fact that true uniformity is never present in all parts of a cast film. Hence a cast film is dependent on the size of the film to meet FDA guidelines.

Ideally, as we will see the film forming materials and the active should be deposited from a separate source and into a well of a fixed size.

An aspect of the present invention is adequate mixing of the drug and film former composition, not from the perspective of uniform distribution of drug in the film, but rather adequately containing the dose of the drug within the final dried film matrix. This means that substantially all of the drug is contained within the film matrix in most embodiments, meaning the drug is substantially subsumed within the film. However, in certain embodiments, the drug will be deposited and remain on the top surface of the film, or remain on the bottom surface of the film. A polymeric binder may be used when the drug is deposited to ensure that it remains adhered to the film.

Mechanical Intervention (Absence of)

Thematically, the Applicants teach low viscosity of the film former composition to form a film in the mold or well. This system teaches away from the high viscosities relied upon for content uniformity equilibrium in cast film.

This patent teaches against the main fundamental of prior film art, namely, the use of high viscosity to prevent migration of the active and preserve uniformity of dose content. Instead, high viscosity here works contrary to the deposition of the film former's dispersion in the well. Accuracy of the active is instead preserved by the direct deposition into the well contains the film former.

By mechanical intervention, we mean physical contact with the film composition to spread the film composition, e.g. a three roll coating apparatus, a doctor blade, or equivalent coating technique.

The high viscosity (and high surface and interfacial tensions) of the prior art (see Watson reference to non-flowing solid/film), required mechanical intervention (via the coating apparatus) to apply as a film. The film compositions of the prior art simply lack the spreading or flow characteristics to make films deposited in wells.

However, it is contemplated that non mechanical compressed air and/or vibration and/or brief ultrasound may be employed to encourage flow of the film composition into a film in the mold or well or surface active agents to reduce surface tension or substrates to reduce contact angle to promote wetting and spreading of film composition.

Printing/Embossing

Once the film is dry, it is possible to print or emboss an identifier on the film dosage form. For printing, individual print heads are typically required. One advantage of the current invention is that printing can be targeted and calibrated in a precise location on the film. Also the well may have a chevron such that it leaves an imprint identity on the dried film.

Multi-Layer Films

Multi layer films are possible with this methodology simply by addition depositions of actives, or additional film compositions in the manufacturing process. For example, a semi insoluble (or insoluble) backing layer may be separately deposited on a deposited film. This may be done after the first layer is dried, or where density and miscibility will permit separate deposit on non-dried layers, on a non-dried layer. Similarly, a special layer of muco-adhesive, permeation enhancers, or other excipients disclosed herein may be deposited separately where desired.

Covering the Mold or Well

It is contemplated that the mold or well will be covered and sealed as part of a continuous manufacturing process. It is important then that consideration be given relative to ambient humidity prior to sealing the mold or well to avoid bringing excess moisture into the package. It may be desirable to cool the film containing well or mold, or use other method (compressed air, nitrogen or other gas) to reduced humidity prior to packaging.

Various forms of guided placement may be employed to ensure alignment of the mold or well with the top covering. In other embodiments, guided placement is not needed, particularly where the top covering is gang printed.

The top covering will typically be foil, aclar, or other suitable sheet like material with suitable barrier properties to ensure stability of the product for the intended area of use (see ICH global guidelines).

The final package may be child resistant. The molds or wells may be joined together in a group of packages or may be separated. Such separation may occur at the time of filling/deposit or later, i.e. after drying.

The Dried Film

Thematically, film formation by deposit presents much more flexibility than conventional wet casting. This is because in conventional wet casting, uniform distribution of active within the film is necessary so that when cut into final pieces the individual film doses will meet drug content label claims.

In contrast, here the desired level of drug is accurately metered into the mold or well along with the film former composition. Drug migration or agglomeration is not really an issue.

The dried film must have only minimal mechanical strength to allow it to be released from the mold or well. A given film formulation's propensity to elongation is acceptable. Tensile strength and elasticity may be minimal.

The dried film must simply be strong enough for release and use by the consumer.

Issues like surface mottle, or voids do not represent drug content defects, and so are judged on the basis of consumer acceptability.

The dried film of the present invention preferably has less than 10% variability in height (measured from the thickest portion of the film to the thinnest portion, measured vertically). In certain embodiments, additional variability may be acceptable or preferred for a wedged or tapered shape.

Preferably, substantially all of the drug is contained within the dried film matrix in most embodiments. However, in certain embodiments, the drug will be deposited and remain on the top surface of the film, or remain on the bottom surface of the film.

Pre-Releasing the Film

In some embodiments, it may be desirable to take steps to pre-release the film from the bottom of the mold or well (such pre release may be in whole or in part). For example, a roller may be employed with a surface that promotes release of the film from the bottom of the mold or well.

This step may occur prior to, or after, the covering is placed in top of the mold or the well. The purpose is to make it easier for the patient to remove the film from the mold or well for use. Vacuum may also be employed for this purpose.

Film-Forming Polymers

The non limiting polymer may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, pullulan, hydroxypropylmethyl cellulose, hydroxyethyl cellulose, hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include, but are not limited to, biodegradable polymers, copolymers, block polymers and combinations thereof. Among the known useful polymers or polymer classes which meet the above criteria are: poly (glycolic acid) (PGA), poly(lactic acid) (PLA), polydioxanoes, polyoxalates, poly(.alpha.-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly (lactic acid), copolymers of .alpha.-amino acids, copolymers of .alpha.-amino acids and caproic acid, copolymers of .alpha.-benzyl glutamate and polyethylene glycol, copolymers of succinate and poly(glycols), polyphosphazene, polyhydroxy-alkanoates and mixtures thereof. Binary and ternary systems are contemplated.

Other specific, but non limiting, polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxy-acetic acid." Four such polymers include lactide/glycolide 100 L, believed to be 100% lactide having a melting point within the range of 338.degree.-347.degree. F. (170.degree.-175.degree. C.); lactide/glycolide 100 L, believed to be 100% glycolide having a melting point within the range of 437.degree.-455.degree. F. (225.degree.-235.degree. C.); lactide/glycolide 85/15, believed to be 85% lactide and 15% glycolide with a melting point within the range of 338.degree.-347.degree. F. (170.degree.-175.degree. C.); and lactide/glycolide 50/50, believed to be a copolymer of 50% lactide and 50% glycolide with a melting point within the range of 338.degree.-347.degree. F. (170.degree.-175.degree. C.).

The Biodel materials represent a family of various polyanhydrides which differ chemically.

Generally, lower molecular weight polymer grades will be favored for certain embodiments of the present invention, as they will make lower viscosity film former compositions.

Such lower molecular weight grades will generally disintegrate faster than higher molecular weight grades. Where longer disintegration times are desired, it may be desirable to include non-water soluble polymers.

Suitable Excipients

Any suitable excipient known in the art may be using in compositions of the present invention. Apart from film formers, a non limiting list includes, pH buffers, permeation enhancers, surfactants, viscosity reducing agents, wetting agents, de-gassing agents, gassing agents, flavors, bitter masking agents, plasticizers, anti-caking agents, co-solvents, antioxidants and any other known excipient.

Excipients may be included in sufficient or effective amounts.

As discussed above, excipients may be added with the film former composition, or the drug (where the two are deposited separately).

Solvents

The following is a non-limiting list of solvents that may be employed: water, ethanol, acetone, DMSO, isopropanol, glycerol, propylene glycol, propylene carbonate, ethyl acetate, d-limonene.

pH Buffers

Buffering agents may be used to control pH (acidic or base), including without limitation, sodium bicarbonate, potassium bicarbonate, sodium carbonate, potassium carbonate, calcium carbonate, dipotassium phosphate, potassium citrate, sodium phosphate, Formic Acid/Sodium Formate, Hydrogen Chloride/Potassium Chloride, Hydrogen Chloride/Glycine, Hydrogen Chloride/Potassium Hydrogen Phthalate, Citric Acid/Sodium Citrate, Acetic Acid/Sodium Acetate, Citric Acid/Disodium Hydrogen Phosphate, Citric Acid/Trisodium Citrate Dihydrate, etc, and any other such buffer system.

The buffer system may be designed to dynamically control the pH of the product taking into consideration the effect of saliva during use, i.e., a dynamic buffer system. Non limitative, examples of buffer systems to obtain a pH include dibasic sodium phosphate and monobasic sodium phosphate. Both are FDA accepted buffer materials used and listed in the inactive ingredients list.

For example, for a pH of 7, the ratio of monobasic/dibasic can be 4.6/8.6; for a pH of 7.5 the ratio of monobasic/dibasic can be 1.9/11.9; and for a pH of 8.0 the ratio of monobasic/dibasic can be 0.6/13.4. These are mathematically calculated buffer numbers and will need to be adjusted according to the other ingredients added to the formula.

They also need to be adjusted for the length of time designed for the dissolution of the dosage unit on the buccal mucosa since saliva can be of a ph of about 6.8 but as it is made in larger amounts in the mouth the ph of saliva can sometimes become more basic. Thus this dynamic buffer range is adjusted in the dosage unit by the amount s of the buffer system since saliva is freshly renewable in the mouth. See Fuisz U.S. Patent Application Publication Nos. 2009/0098192 A1 and US 2011/0318390 A1 discussing dynamic buffering and incorporated herein by reference. The dynamic buffer systems of the present invention may be acidic or basic.

Surfactants

Surfactants may be useful in connection with the present invention to reduce surface tension. Reducing surface tension is helpful to promote flowability of the film composition (see Young Equation discussed above), and may also be useful to promote mixing of the film former composition with separately added drug.

Non limiting surfactants may include non-ionic surfactants, like polyol esters (e.g. glycol or glycerol esters, sorbitan derivatives); polyoxyethylene esters (e.g. polyethylene glycol (the "PEGs"; and poloxamers. Common ionic surfactants include ethers of fatty alcohols.

Any suitable surfactant may be employed.

In the approach of Yang et al, too much surfactant will create a product with a contact angle that is too low (Young's Equation) for coating on the substrate. Here, the formulator will want to use more surfactant to decrease the contact angle and promote flowability.

Permeation Enhancers

The film made by deposit may comprise one or more penetration agents, i.e., a substance that enhances absorption through the mucosa, mucosal coating and epithelium (otherwise known (see U.S. Patent Application Publication No. 2006/0257463 A1, the content of which is incorporated herein by reference) as a "penetration enhancer" or "permeability enhancer"). The penetration agent may comprise but is not limited to polyethylene glycol (PEG), diethylene glycol monoethyl ether (Transcutol), 23-lauryl ether, aprotinin, azone, benzalkomin chloride, cetylperidium chloride, cetylmethylammonium bromide, dextran sulfate, lauric acid, lauric acid/propylene glycol, lysophosphatilcholine, menthol, methoxysalicylate, oleic acid, phosphaidylcholine, polyoxyethylene, polysorbate 80, sodium EDTA, sodium glycholated, sodium glycodeoxycholate, sodium lauryl sulfate, sodium salicylate, sodium taurocholate, sodium taurodeoxycholate, sulfoxides, and various alkyl glycosides or, as described in U.S. Patent Application Publication No. 2006/0257463, bile salts, such as sodium deoxycholate, sodium glycodeoxycholate, sodium taurocholate and sodium glycocholate, surfactants such as sodium lauryl sulfate, polysorbate 80, laureth-9, benzalkonium chloride, cetylpyridinium chloride and polyoxyethylene monoalkyl ethers such as the BRIJ® and MYRJ® series, benzoic acids, such as sodium salicylate and methoxy salicylate, fatty acids, such as lauric acid, oleic acid, undecanoic acid and methyl oleate, fatty alcohols, such as octanol and nonanol, laurocapram, the polyols, propylene glycol and glycerin, cyclodextrins, the sulfoxides, such as dimethyl sulfoxide and dodecyl methyl sulfoxide, the terpenes, such as menthol, thymol and limonene, urea, chitosan and other natural and synthetic polymers. Preferably, the penetration agent is a polyol, e.g., polyethylene glycol (PEG), glycerin, maltitol, sorbitol etc. or diethylene glycol monoethyl ether (Transcutol).

Preferably, the dried film composition may comprise 0.01% to 10% permeation enhancer by mass, more preferably 0.1% to 5%.

Viscosity Reducing Agents

Various agents may be employed to reduced viscosity. In particular and without limitation, hydrophobic salts may serve to reduce viscosity, which is of use in connection with the film former composition. Without limitation, the following agents have been found useful: arginine hydrochloride, sodium thiocyanate, ammonium thiocyanate, ammonium sulfate, ammonium chloride, calcium chloride, zinc chloride, or sodium acetate. The teaching of US 20150071925, hereby incorporated herein as if fully stated. Organic esters may also be useful. See US 20150071925, hereby incorporated herein as if fully stated.

Effective amounts are used.

Anti-Caking Agents

Anti-Caking Agents are particularly useful where the drug active is added separately from the firm former composition in powder or particulate form.

Moisture, pressure and temperature all adversely affect powdered and granulated products. These conditions can make products cake, lump, bridge, clog equipment and cause fib and performance problems. Anti-caking and Free-flow powder agents can improve the flow behavior and storage stability of a broad variety of food products.

Silica derived materials are preferred.

A non limitative list includes: tricalcium phosphate, powdered cellulose, magnesium stearate, sodium bicarbonate, sodium ferrocyanide, potassium ferrocyanide, calcium ferrocyanide, bone phosphate, sodium silicate, silicon dioxide, calcium silicate, magnesium trisilicate, talcum powder, sodium aluminosilicate, potassium aluminium silicate, calcium aluminosilicate, bentonite, aluminium silicate, stearic acid, and polydimethylsiloxane.

Effective amounts are employed for reliable flow of powder/particulate.

Pharmaceutical Actives (Also Referred to Herein as Active Pharmaceutical Ingredients or Drugs)

By the term pharmaceutical active agent, we mean a drug as described below. By pharmaceutical active agent composition, we mean any composition containing one or more pharmaceutical active agents. However, it is expressly contemplated that the compositions and methods taught herein are not limited to drugs but may include any active agent as more fully described below.

The active agents that may be incorporated into the films of the present invention include, without limitation bioactive agents such as pharmaceutical active agents, cosmetic active agents, drugs, medicaments, botanicals, antigens or allergens such as ragweed pollen, spores, microorganisms, plant actives, enzymes and vitamins, as well asother active agents such as seeds, mouthwash components, flavors, fragrances, preservatives, sweetening agents, colorants, spices, and combinations thereof. An active agent composition is a composition containing one or more of the active agents described herein.

A wide variety of non limiting medicaments, bioactive active substances and pharmaceutical compositions may be included in the dosage forms of the present invention.

Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, antianxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, uterine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (available as Oxycontin®), ibuprofen, aspirin, acetaminophen, and combinations thereof that may optionally include caffeine.

Other preferred drugs for other preferred active ingredients for use in the present invention include anti-diarrheals such as immodium AD, anti-histamines, anti-tussives, decongestants, vitamins, and breath fresheners. Common drugs used alone or in combination for colds, pain, fever, cough, congestion, runny nose and allergies, such as acetaminophen, chlorpheniramine maleate, dextromethorphan, pseudoephedrine HCl and diphenhydramine may be included in the film compositions of the present invention.

Also contemplated for use herein are anxiolytics such as alprazolam (available as Xanax®); anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as loratadine (available as Claritin®), astemizole (available as Hismanal™), nabumetone (available as Relafen®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®); anti-migraines such as Imigra®, ACE-inhibitors such as enalaprilat (available as Vasotec®), captopril (available as Capoten®) and lisinopril (available as Zestril®); anti-Alzheimer's agents, such as nicergoline; and Ca.sup.H-antagonists such as nifedipine (available as Procardia® and Adalat®), and verapamil hydrochloride (available as Calan®).

Erectile dysfunction therapies include, but are not limited to, drugs for facilitating blood flow to the penis, and for effecting autonomic nervous activities, such as increasing parasympathetic (cholinergic) and decreasing sympathetic (adrenersic) activities. Useful non-limiting drugs include sildenafils, such as Viagra®, tadalafils, such as Cialis®, vardenafils, apomorphines, such as Uprima®, yohimbine hydrochlorides such as Aphrodyne®, and alprostadils such as Caverject®.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Botanicals may be employed, including marijuana, tobacco and any derivative thereof, including tetrahydrocannabinol and cannabidiol). Such botanicals may or may not be approved for pharmaceutical use or otherwise understood to be pharmaceutically active.

An anti-oxidant may also be added to the film to prevent the degradation of an active, especially where the active is photosensitive.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like. Anti tartar agents for dental use may also be employed.

Coloring Agents

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

The films containing flavorings may be added to provide a hot or cold flavored drink or soup.

These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

When the active is combined with the polymer in the solvent, the type of matrix that is formed depends on the solubilities of the active and the polymer. If the active and/or polymer are soluble in the selected solvent, this may form a solution. However, if the components are not soluble, the matrix may be classified as an emulsion, a colloid, or a suspension.

Transdermal Films

In certain embodiments, the deposit method of the present invention may be used to make transdermal films. Since transdermal films are typically multilayer, different layers may be deposited in series, if necessary between drying intervals. Backing layers of materials not readily depositable may be inserted into the mold or well (including inter alia microneedles). The following patents, describing transdermal compositions, are incorporated by reference as if fully stated herein (including incorporations into such patents) U.S. Pat. No. 9,089,527 B2 (assigned to Lohmann), U.S. Pat. No. 8,696,637 (assigned to Lohmann), U.S. Pat. No. 6,117,448 (assigned to Lohmann), U.S. Pat. No. 5,820,876 (assigned to Lohmann). Obviously, different compositions, and excipients are used in transdermal systems from oral soluble films and so the teaching of the incorporate patents is important for such embodiments.

EXAMPLES

A number of template molds were made, 10 mil recess thick, and adhered to a Teflon sheet. The compositions are shown in Table 1A, and Table 2A and Table 3. Results after deposit and drying for the compositions of Table 1A and Table 2A, are found in Tables 1B and 2B, respectively.

As the results in Table 1B demonstrate, the compositions described in Table 1A were generally too viscous and exhibited too much surface tension to adequately flow into a mold.

A number of the examples of 2A successfully flowed into films, and a certain examples demonstrated good embedding of solids. For example, sample D of Table 2A showed good embedding of calcium carbonate particulate, which was used as a "dummy" drug particulate. The flowability of these examples would preclude their ability to be coated using conventional wet casting techniques. Their very proclivity to flow would lead them to roll off the substrate in a conventional casting process.

The compositions of Table 3 are non-aqueous. Sample NA4, comprising 29.7% PEO (300,000) and 70.3% PEG400 is a promising approach for a slow release film of the present invention. Applicants observed that a range of 20-40% PEO (300,000 mw and above), together with PEG 80 as a solvent may be an attractive formulation option where slow release is desired from a film made by the deposit method.

Table 4 contains surface tension values.

TABLE 1A

Aqueous Evaluation Samples

| Sample ID | Instagel | Corn Starch | HPMC K15M | HPMC F50 | HPC | PVP | PG | PEG2000 |
|---|---|---|---|---|---|---|---|---|
| 1 | 1.45% | 1.99% | | | | | | |
| 2 | 9.15% | | | | | | | |
| 3 | | 4.32% | | 6.81% | | 4.48% | | 8.16% |
| 4 | | 3.74% | | 5.79% | | 2.23% | 6.83% | |
| 5 | | | | 2.57% | | | 1.05% | |
| 6 | | | 5% | | | | | |
| 7 | | | 1.25% | | | | | |
| 8 | | | 1.00% | | | | | |
| 9 | | | | | 1.86% | | | |
| 10 | | | | | 0.90% | | | |

TABLE 1B

Aqueous Evaluation Samples Post Thermal Treatment

| Sample ID | Pass | Fail | Cause |
|---|---|---|---|
| 1 | | x | high contact angle on silicon mold, did not wet or spread, did not embed solids, does not disperse in water |
| 2 | | x | high contact angle on silicon mold, did not wet or spread, did not embed solids, does not disperse in water |
| 3 | | x | too viscous |
| 4 | | x | very viscous, produced thick film that did not disperse readily in water |
| 5 | | x | film very thin and brittle, poor wetting and spreading on substrate, strong adhesion to teflon substrate when dried |
| 6 | | x | too viscous |
| 7 | | x | film too brittle and too thin |
| 8 | | x | film too brittle and too thin |
| 9 | | x | too viscous to add to template |
| 10 | | x | too viscous to add to template |

TABLE 2A

Aqueous PEO Film Former Compositions

| Sample ID | PEO 100K | PEO 300K | PEO 900K | PEG400 | PG | PS 20 | Viscosity cps |
|---|---|---|---|---|---|---|---|
| A | | | 9.09% | 18.18% | | | |
| B | 10.58% | | | 6.68% | | | 331* |
| C | 10.59% | | | | 7.30% | | 366* |
| D | 10.69% | | | 5.59% | | | 306* |
| E | 4.76% | | | | | | |
| F | | | 6.52% | 12.90% | | 1.65% | |
| G | | 5.71% | | | 3.50% | | 2243-1261** |
| H | | 5.79% | | 4.05% | | | |
| I | 18.31% | | | | 7.44% | | 1846-1155** |
| J | 18.31% | | | 8.80% | | | |
| K | 12.38% | | | | 4.45% | | 413* |
| L | 10.53% | | | 5.61% | | | |
| M | 7.06% | 1.77% | | | 5.60% | | |
| N | | 4.76% | | | | | 653-468** |
| O | | 3.67% | | | | | 217* |
| P | | 6.28% | | | | | |

*Newtonian fluid viscosity

**Non-Newtonian fluid viscosity range from 10 to 100 s$^{-1}$

TABLE 2B

Aqueous PEO Film Former Post Thermal Treatment Evaluations

| Sample ID | Pass | Fail | Cause |
|---|---|---|---|
| A | x | | films .2 mm think easily disperse in water |
| B | x | | good spreading and wetting, low viscosity |
| C | x | | good spreading and wetting, low viscosity |
| D | x | | film former added to calcium carbonate, good embedding of solids |
| E | x | | viscous, but good spreading and wetting, thin film easily disperses in water |
| F | x | | viscous, films .15 mm, easily disperse in water |
| G | x | x | viscous composition, can produce good thin film, readily dispersibled in water |
| H | x | x | viscous composition, can produce good film, easily dispersible in water |
| I | | x | too viscous, thick film, not easily dispersible in water |
| J | | x | too viscous, thick film, not easily dispersible in water |
| K | x | | good spreading and wetting, low viscosity |
| L | x | | good spreading and wetting, low viscosity |
| M | x | | good spreading and wetting, low viscosity |
| N | x | | produced film with good dissolution in water |
| O | x | | produced thin film with good dissoution in water |
| P | x | | produced thin film easily dispersible in water |

TABLE 3

Non-Aqueous PEO Compositions Post Thermal Treatment 90° C.

| Sample ID | PEO100K | PEO300K | PEG400 | Pass | Fail | Cause |
|---|---|---|---|---|---|---|
| NA1 | 8.88% | | 91.12% | | x | lacks cohesion, waxy dispersion |
| NA2 | 9.51% | | 90.49% | | x | lacks cohesion, waxy dispersion |
| NA3 | | 10.22% | 89.78% | | x | weak, wet, thick (1.23 mm) and fragile film; poor dissoution in water |
| NA4 | | 29.70% | 70.30% | x | x | viscous dispersion, poor flowability, opaque thick (1.6 mm) strong film; slow dissolution in water, tacky vehicle when wet |

TABLE 4

Examples of Surface Tension Values

| | Temp ° C. | γ mN/m |
|---|---|---|
| water | 25 | 71.97 |
| | 40 | 69.56 |
| | 80 | 62.6 |
| PEG200 | 20 | 43.5 |
| ISP | 25 | 23 |

What is claimed is:

1. A method of making an oral soluble film containing at least one active agent, comprising:
   continuously stirring a suspension of a film forming composition and particulates of at least one active agent in a tank;
   depositing the suspension of the film forming composition and the particulates of the at least one active agent separately into each of a plurality of wells while continuously stirring the suspension in the tank, the suspension of the film forming composition and the particulates of the at least one active agent having a yield stress of less than 30 Pa and forming a contact angle with the well of less than 90°, wherein the suspension of the film forming composition and the particulates of the at least one active agent flows into a film in the well within 20 seconds and has a viscosity below 600 centipoise; and
   drying the film using hot air currents.

2. The method according to claim 1, wherein the suspension of the film forming composition and at least one active agent flows into a film in the well within 5 seconds.

3. The method according to claim 1, wherein the suspension of the film forming composition and at least one active agent flows into a film in the well within 1 second.

4. The method according to claim 1, wherein the suspension of the film forming composition and at least one active agent has a yield stress of less than 15 Pa.

5. The method according to claim 1, wherein the suspension of the film forming composition and at least one active agent has a viscosity below 300 centipoise.

* * * * *